(12) United States Patent
Ikeuchi et al.

(10) Patent No.: US 9,115,235 B2
(45) Date of Patent: Aug. 25, 2015

(54) WATER ABSORBING AGENT AND PRODUCTION METHOD THEREOF

(75) Inventors: Hiroyuki Ikeuchi, Hyogo (JP); Shigeru Sakamoto, Hyogo (JP); Sayaka Machida, Hyogo (JP); Katsuyuki Wada, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 676 days.

(21) Appl. No.: 12/295,495

(22) PCT Filed: Aug. 31, 2007

(86) PCT No.: PCT/JP2007/067455
§ 371 (c)(1),
(2), (4) Date: Sep. 30, 2008

(87) PCT Pub. No.: WO2008/026783
PCT Pub. Date: Mar. 6, 2008

(65) Prior Publication Data
US 2009/0182294 A1    Jul. 16, 2009

(30) Foreign Application Priority Data
Aug. 31, 2006   (JP) ................... 2006-236001

(51) Int. Cl.
| | | |
|---|---|---|
| *C08F 36/14* | (2006.01) | |
| *C08F 220/00* | (2006.01) | |
| *A61L 15/60* | (2006.01) | |
| *B01J 20/26* | (2006.01) | |

(52) U.S. Cl.
CPC ............... *C08F 220/00* (2013.01); *A61L 15/60* (2013.01); *B01J 20/267* (2013.01)

(58) Field of Classification Search
USPC .......... 524/430, 436, 437, 444, 447; 502/400, 502/401; 604/358; 525/328.3
See application file for complete search history.

(56) References Cited

U.S. PATENT DOCUMENTS

| | | | |
|---|---|---|---|
| 38,444 | A | 5/1863 | Douglas |
| 4,732,968 | A | 3/1988 | Obayashi et al. |
| 5,149,335 | A | 9/1992 | Kellenberger et al. |
| 5,599,335 | A | 2/1997 | Goldman et al. |
| 5,601,542 | A | 2/1997 | Melius et al. |
| 5,652,292 | A | 7/1997 | Stanley, Jr. |
| 5,669,894 | A | 9/1997 | Goldman et al. |
| 5,797,893 | A | 8/1998 | Wada et al. |
| 6,300,275 | B1 | 10/2001 | Weir |
| 6,414,214 | B1 | 7/2002 | Engelhardt et al. |
| 6,831,142 | B2 | 12/2004 | Mertens et al. |
| 6,849,665 | B2 | 2/2005 | Frenz et al. |
| 6,930,221 | B1 | 8/2005 | Strandqvist |
| 7,098,284 | B2 | 8/2006 | Torii et al. |
| 7,638,570 | B2 * | 12/2009 | Torii et al. ............ 524/430 |
| 2003/0181115 | A1 | 9/2003 | Nagasuna et al. |
| 2004/0019342 | A1 | 1/2004 | Nagasuna et al. |
| 2004/0106745 | A1 | 6/2004 | Nakashima et al. |
| 2005/0209352 | A1 | 9/2005 | Dairoku et al. |
| 2008/0139693 | A1 * | 6/2008 | Ikeuchi et al. .......... 523/111 |
| 2008/0269372 | A1 | 10/2008 | Dairoku et al. |
| 2009/0036855 | A1 | 2/2009 | Wada et al. |
| 2009/0281232 | A1 * | 11/2009 | Ikeuchi et al. .......... 524/556 |

FOREIGN PATENT DOCUMENTS

| | | |
|---|---|---|
| CN | 1635914 A | 7/2005 |
| CN | 1903893 | 1/2007 |
| EP | 0314825 | 5/1989 |
| EP | 0493011 | 7/1992 |
| EP | 1616581 | 1/2006 |
| JP | 62-132936 | 6/1987 |
| JP | 01-156302 | 6/1989 |
| JP | 06000370 | 1/1994 |
| JP | 07-025935 | 1/1995 |
| JP | 2004-001355 | 1/2004 |
| JP | 2004-261797 | 9/2004 |
| JP | 2006-068731 | 3/2006 |
| JP | 2006143972 | 6/2006 |
| WO | 93/24153 | 12/1993 |
| WO | 9526209 | 10/1995 |
| WO | 2004069915 | 8/2004 |
| WO | 2005/075070 | 8/2005 |

OTHER PUBLICATIONS

Japanese Office Action dated Feb. 4, 2014, from the Japanese Patent Office in JP Application No. 2007-558365, and English translation thereof.
Decision to Grant dated Jul. 15, 2014, from the Japanese Patent Office in corresponding JP Application No. 2007-558365, and English translation thereof.

* cited by examiner

*Primary Examiner* — Monique Peets
(74) *Attorney, Agent, or Firm* — Roylance, Abrams, Berdo & Goodman, L.L.P.

(57) ABSTRACT

A water absorbing agent includes water absorbent resin particles which are obtained by polymerizing a water-soluble ethylenic unsaturated monomer and which internally include a cross-linked structure, wherein a pressurized void average radius index is 140 or more. As a result, it is possible to provide a water absorbing agent which essentially includes water absorbent resin particles and is suitable for use in a sanitary material. Specifically, it is possible to improve not only a performance for absorbing and retaining aqueous liquid without pressure or under pressure but also (i) a performance for quickly absorbing aqueous liquid with a great help of a performance of a fibrous material, (ii) a performance for dispersing the aqueous liquid after absorbing the aqueous liquid, and (iii) a performance for retaining the aqueous liquid after absorbing the aqueous liquid.

24 Claims, 3 Drawing Sheets

F I G. 3
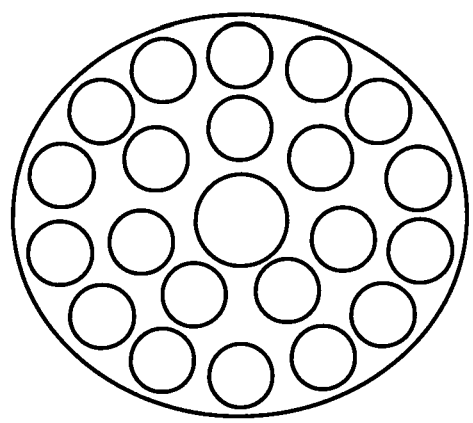

WATER ABSORBING AGENT AND PRODUCTION METHOD THEREOF

TECHNICAL FIELD

The present invention relates to a water absorbing agent and a production method thereof. More specifically, the present invention relates to (i) a water absorbing agent favorably used for a sanitary material such as a diaper and (ii) a production method of the water absorbing agent.

BACKGROUND ART

Conventionally, due to a high absorption rate with respect to aqueous liquid, a great absorption amount, and a great retention property, a water absorbent resin is blended with a fibrous material as necessary so as to constitute an absorbent core of a sanitary material for a purpose of use in a sanitary material such as a diaper.

Recently, with requirement for reduction in thickness of a sanitary material such as a diaper, a ratio of the water absorbent resin in the absorbent core is likely to increase (concentration is likely to be higher) (for example, see Patent Documents 1 to 3). As performances of the water absorbent resin used in the higher-concentration absorbent core in which the ratio of the water absorbent resin is high, an inter-particle void average radius at the time of saturation and swelling without pressure and an inter-particle void average radius at the time of saturation and swelling under pressure are defined (see Patent Documents 4 and 5). Besides, a large number of water absorbent resins suitable for use with high concentration have been proposed (see Patent Documents 6 to 15). However, there is a case where even the water absorbent resin satisfying the proposed properties does not sufficiently meet the requirement in terms of its performance at the occasion of use in a more highly concentrated sanitary material such as a diaper.

[Patent Document 1]
　International Publication No. 95/26209 Pamphlet
[Patent Document 2]
　U.S. Pat. No. 5,669,894
[Patent Document 3]
　U.S. Pat. No. 5,599,335
[Patent Document 4]
　Japanese Unexamined Patent Publication No. 290290/2003 (Tokukai 2003-290290)
[Patent Document 5]
　U.S. Unexamined Patent Publication No. 2003-0181115
[Patent Document 6]
　U.S. Pat. No. 5,149,335
[Patent Document 7]
　U.S. Pat. No. 5,601,542
[Patent Document 8]
　U.S. Pat. No. 6,414,214
[Patent Document 9]
　U.S. Pat. No. 6,849,665
[Patent Document 10]
　U.S. Pat. No. 7,098,284
[Patent Document 11]
　U.S. Reissue Pat. No. 38444
[Patent Document 12]
　U.S. Pat. No. 5,797,893
[Patent Document 13]
　U.S. Pat. No. 6,300,275
[Patent Document 14]
　U.S. Pat. No. 6,831,142
[Patent Document 15]
　U.S. Pat. No. 6,930,221

DISCLOSURE OF INVENTION

Problems to be Solved

With increase in the ratio of the water absorbent resin in the absorbent core, it is required to develop a water absorbing agent which has both a performance of the conventional water absorbent resin and a performance of the fibrous material of the conventional absorbent core as a future water absorbent resin.

As the performances required in the water absorbing agent, there are not only a performance for absorbing and retaining aqueous liquid without pressure or under pressure but also (i) a performance for quickly absorbing the aqueous liquid with a great help of the performance of the fibrous material, (ii) a performance for dispersing the aqueous liquid after absorbing the aqueous liquid, and (iii) a performance for retaining the aqueous liquid after absorbing the aqueous liquid. Particularly in a highly concentrated absorbent core, a water absorbent resin having absorbed aqueous liquid is required to have higher performances due to its larger volume and deformation caused by pressure.

An object of the present invention is to provide a water absorbing agent suitable for a purpose of use in a sanitary material having the aforementioned performances and for other purpose of use.

Means to Solve the Problems

The inventors of the present invention diligently studied in order to solve the foregoing problems. As a result of the diligent study, they found that a conventionally unachievable void radius between gel particles under pressure after absorption of aqueous liquid under pressure is important in a water absorbing agent essentially including water absorbent resin particles, and they also found a technique for enhancing the performances to a level which cannot be achieved by the conventional arts, thereby completing the present invention.

That is, a water absorbing agent, comprising water absorbent resin particles which are obtained by polymerizing a water-soluble ethylenic unsaturated monomer and which internally include a cross-linked structure, wherein a pressurized void average radius index is 140 or more, where the pressurized void average radius index is a swollen gel void radius (d50) corresponding to 50% of a cumulative void water content in a physiological saline water under a load of 2.07 kPa.

Further, a water absorbing agent according to the present invention comprising water absorbent resin particles which are obtained by polymerizing a water-soluble ethylenic unsaturated monomer and which internally include a cross-linked structure, wherein a pressurized void average radius index is 100 or more.

In the water absorbing agent according to the present invention, the pressurized void average radius index is a swollen gel void radius (d50) corresponding to 50% of a cumulative void water content in a physiological saline water under a load of 2.07 kPa.

Further, a water absorbing agent according to the present invention includes water absorbent resin particles which are obtained by polymerizing a water-soluble ethylenic unsaturated monomer and which internally include a cross-linked structure, wherein 90 wt % or more of the water absorbing agent obtained by reversed phase suspension polymerization is particles whose particle diameter ranges from 150 to 850

μm, and the water absorbing agent includes an agent for enhancing a pressurized void average radius index.

Further, the water absorbing agent is particulate, and 90 wt (mass) % or more of the water absorbing agent is particles whose particle diameter ranges from 150 to 850 μm. Further, the absorbency against pressure (AAP) is 10 g/g or more where the pressure is 4.83 kPa. Further, a surface of the water absorbent resin particles is cross-linked, and the water absorbing agent includes an agent for enhancing a pressurized void average radius index.

Further, it is preferable to arrange the water absorbing agent so that a mass average particle diameter (D50) ranges from 200 to 500 μm, and a logarithmic standard deviation (σζ) of a particle size distribution ranges from 0.25 to 0.45, and a bulk specific gravity (g/ml) ranges from 0.72 to 1.00.

Further, it is preferable to arrange the water absorbing agent so that an absorbency against pressure (AAP) ranges from 20 g/g to 29 g/g where the pressure is 4.83 kPa, and a difference between a centrifuge retention capacity (CRC) and the absorbency against pressure (AAP) is 7 g/g or less.

Further, it is preferable to arrange the water absorbing agent so that the water absorbent resin is particulate, and it is preferable to arrange the water absorbing agent so that the water absorbent resin is in a granulated manner.

Further, a method according to the present invention for producing a water absorbing agent comprises the steps of: cross-linking and polymerizing an unsaturated monomer aqueous solution containing acrylic acid and/or salt thereof as a main component in the presence of an internal cross-linking agent so as to obtain water absorbent resin particles; drying the water absorbent resin particles after the step of cross-linking and polymerizing the unsaturated monomer aqueous solution, so as to satisfy the following conditions (a) to (c) in the water absorbent resin particles; and carrying out, with respect to the water absorbent resin particles, a treatment for enhancing a pressurized void average radius index, wherein
  (a) a mass average particle diameter (D50) ranges from 150 to 500 μm,
  (b) a logarithmic standard deviation (σζ) of a particle size distribution ranges from 0.25 to 0.45, and
  (c) a bulk specific gravity (g/ml) ranges from 0.72 to 1.00.

Further, it is preferable to arrange the method so as to include the step of carrying out a surface cross-linking treatment with respect to a surface of the water absorbent resin particles after the step of drying the water absorbent resin particles.

Further, a method according to the present invention for producing a water absorbing agent, comprising the steps of: cross-linking and polymerizing an unsaturated monomer aqueous solution containing acrylic acid and/or salt thereof as a main component in a hydrophobic organic solvent by reversed phase suspension polymerization so as to obtain water absorbent resin particles; drying the water absorbent resin particles; carrying out a surface cross-linking treatment; and adding to the water absorbent resin particles an agent for enhancing a pressurized void average radius index.

Further, it is preferable to arrange the method so that the agent for enhancing a pressurized void average radius index is at least one kind selected from a multivalent metal compound, a polycation compound, and inorganic fine particles.

Further, it is preferable to arrange the method so that 90 wt % or more of the water absorbent resin particles is particles whose particle diameter ranges from 150 to 850 μm.

Further, it is preferable to arrange the method so that (i) a polymerizable cross-linking agent having two or more polymerizable unsaturated groups and (ii) a reactive internal cross-linking agent having two or more covalent binding groups or an ionic bonding group is used together as the internal cross-linking agent.

Further, it is preferable to arrange the method so that the water absorbent resin particles in or after carrying out the surface cross-linking treatment satisfy the following conditions (a) to (c), where (a) a mass average particle diameter (D50) ranges from 200 to 500 μm, (b) a logarithmic standard deviation (σζ) of a particle size distribution ranges from 0.25 to 0.45, and (c) a bulk specific gravity (g/ml) ranges from 0.72 to 1.00.

Further, it is preferable to arrange the method so that the agent for enhancing a pressurized void average radius index contains any one of bivalent, trivalent, and tetravalent metal salts.

Further, an absorbing article comprising the water absorbing agent according to the present invention, wherein the absorbing article absorbs urine, feces, or blood.

Effects of the Invention

According to the present invention, the water absorbing agent according to the present invention constitutes an absorbent core of a sanitary material such as a diaper for example, so that it is possible to more widely disperse aqueous liquid in a sandwich core in which the water absorbing agent is densely included or in a high concentration core in which a ratio of the included water absorbing agent is high. Further, it is possible to realize remarkable effect such as production of a thinner sanitary material or a similar effect in use for a sanitary material or other use.

BRIEF DESCRIPTION OF DRAWINGS

FIG. 3 is a cross sectional view illustrating a bottom of a piston.

REFERENCE NUMERALS

Figure 1:
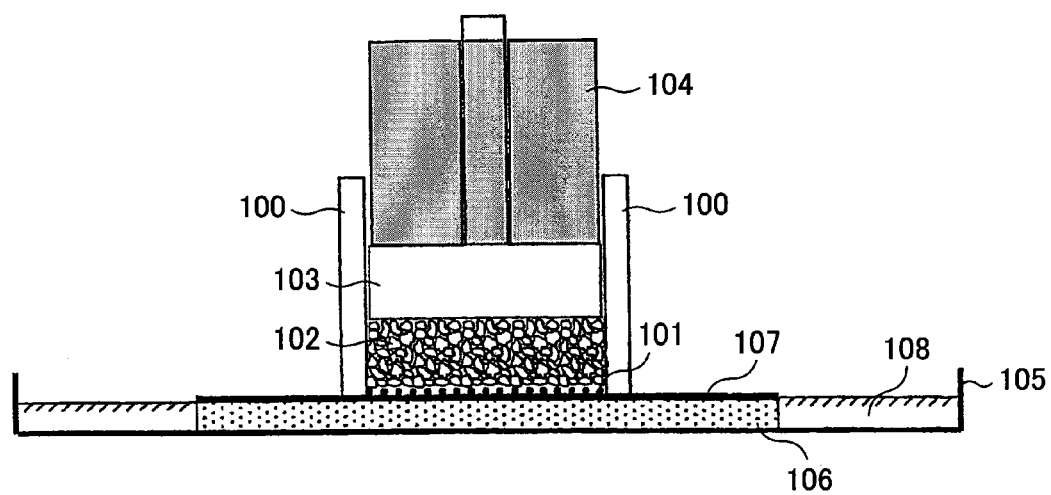
FIG. 1 is a cross sectional view schematically illustrating a measuring device used to measure AAP.

100 Plastic supporting cylinder
101 Stainless 400-mesh metal gauze
102 Water absorbent resin
103 Piston
104 Load (weight)
105 Petri dish
106 Glass filter
107 Filter paper
108 Physiological saline water
201 Filter funnel
202 Glass filter particle No. #3: Average particle diameter ranges from 20 to 30 μm
203 Conduit
204 Liquid tank
205 Clamp
206 Physiological saline water (0.9 wt % sodium chloride aqueous solution)
207 Scale
208 Automatic Elevator
209 Target sample
210 Computer
211 Piston
212 Weight

BEST MODE FOR CARRYING OUT THE INVENTION

The following details the present invention, but the present invention is not limited to the following description of the embodiments and may be suitably altered so as not to depart from the spirit of the present invention.

Note that, in the following explanations, "weight" is synonymous with "mass", "wt %" is synonymous with "mass %". Moreover, a range "A to B" is a range not less than A but not more than B.

(Water Absorbent Resin Particles and Water Absorbing Agent)

Water absorbent resin particles usable in the present invention are water-insoluble water-swelling hydrogel formation polymer (water absorbent resin particles) which is obtained by polymerizing water-soluble ethylenic unsaturated monomer and which internally includes a cross-linked structure. The water-swelling means a state in which absorbency is 10-fold or more, and the water-insoluble means a state in which an amount of a soluble content is preferably 50 wt (mass) % or less, more preferably 20 wt % or less, still more preferably in a below described range. Further, at least an absorbency with respect to a physiological saline water is 10-fold or more. These measurement methods are defined in the present specification.

Examples of a particle shape include a spherical shape, a ball-agglomerated shape, an oblate ball shape, an irregularly-pulverized shape, a granulated irregularly-pulverized-substance shape, and a porous foam shape. Note that, in the present invention, the water absorbent resin particles are sometimes referred to merely as a water absorbent resin.

Further, the resultant water absorbent resin particles may be ground. In grinding the water absorbent resin particles, a conventionally known grinding device such as a homogenizer exemplified in U.S. Pat. No. 6,562,879 can be used.

The water absorbing agent of the present invention refers to an aqueous liquid absorbing and solidifying agent which includes the water absorbent resin as a main component and also includes a small amount or a minute amount of additive or water as necessary. With respect to the whole water absorbing agent, an amount of the water absorbent resin preferably ranges from 70 to 100 wt %, more preferably from 80 to 100 wt %, more preferably from 90 to 100 wt %. As the small amount or minute amount of substance, it is general to essentially use water as a main component thereof, and also a below-described agent for enhancing a pressurized void average radius index and additives are used.

Note that, the aqueous liquid is not limited to water and may be urine, blood, feces, waste fluid, moisture, vapor, ice, a mixture of water and organic solvent, a mixture of water and inorganic solvent, rain water, ground water, and the like, as long as the aqueous liquid includes water. It is preferable that the water absorbing agent is an absorbing and solidifying agent which absorbs and solidifies urine, particularly human urine, out of the aforementioned aqueous liquids.

Specific examples of the water-insoluble water-swelling hydrogel formation polymer or particles thereof include: a partially neutralized cross-linked polyacrylic acid polymer (U.S. Pat. No. 4,625,001, U.S. Pat. No. 4,654,039, U.S. Pat. No. 5,250,640, U.S. Pat. No. 5,275,773, European Patent No. 456136, and the like); a cross-linked partially neutralized starch-acrylic acid graft polymer (U.S. Pat. No. 4,076,663); an isobutylene-maleic acid copolymer (U.S. Pat. No. 4,389,513); a saponified vinyl acetate-acrylic acid copolymer (U.S. Pat. No. 4,124,748); a hydrolyzed acrylamide (co)polymer (U.S. Pat. No. 3,959,569); a hydrolyzed acrylonitril copolymer (U.S. Pat. No. 3,935,099); and the like.

(Pressurized Void Average Radius Index and Measurement Principle Thereof)

In the present invention, the pressurized void average radius index refers to a radius of a void between gel particles under pressure after the water absorbent resin (and the water absorbing agent) absorbs liquid.

Conventionally, it was pointed out that, in case where a ratio of the water absorbent resin used is high, a radius of a void between gel particles is important. As to the water absorbent resin (and the water absorbing agent) used in an absorbent core of a sanitary material such as a diaper, the inventors of the present invention diligently studied performances (reduction of liquid leakage and liquid dispersion) of a diaper or the like in practical use. As a result, they found that: in the performance of the diaper, a diameter of a void between gel particles under pressure (pressurized void average radius index) corresponding to practical use is particularly important.

Further, as to the water absorbing agent in the present invention, its pressurized void average radius index is a range which cannot be obtained in accordance with any conventional techniques. Further, the inventors found that the novel pressurized void average radius index is achieved by below-described means (particle size, polymerization, additive, and the like) which are not disclosed by Patent Documents 1 to 15. Thus, by using the water absorbing agent of the present invention in an absorbent core of a sanitary material such as a diaper, it is possible to more widely disperse aqueous liquid in a sandwich core in which the water absorbing agent is densely included or in a high concentration core in which a ratio of the included water absorbing agent is high, thereby reducing urine leakage in practical use and effectively utilizing the absorption core in a diaper. Thus, it is possible to avoid frequent change of diapers.

The following explains a principle in measuring the pressurized void average radius index.

A height to which a liquid rises up through a capillary having a radius R due to a capillary force is represented by "h". A surface tension of the liquid is represented by "$\gamma$". A contact angle is represented by "$\theta$". A gravitational constant is represented by "g". A density of liquid is represented by "$\rho$". In this way, the pressurized void average radius index is expressed as $h = 2\gamma \cos \theta / \rho g R$ (P. K. Chatterjee, B. S. Gupta, "TEXTILE SCIENCE AND TECHNOLOGY 13 ABSORBENT TECHNOLOGY 2002" (ELSEVIER), page 428, Expression (35)).

Figure 2:
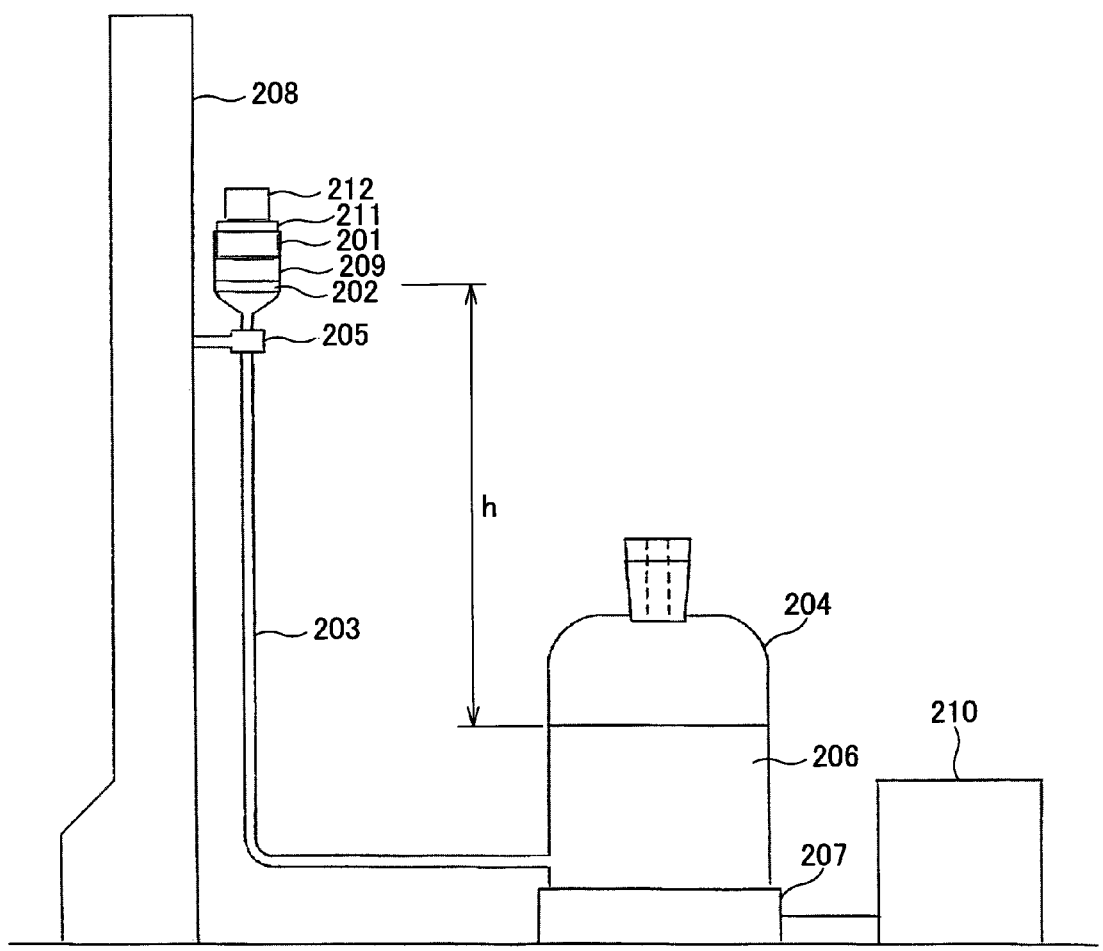
FIG. 2 is a cross sectional view schematically illustrating a measuring device used to measure a pressurized void average radius index.

In a device of FIG. 2, a head difference between a liquid surface level of a liquid tank and a glass filter of a filter funnel is increased from 0 to h (cm), so that liquid in gel particles or a void of the absorbent core in a swollen gel or the absorbent core is partially retained by a void having a diameter greater than a capillary radius (gap) R ($\mu$m) and the retained water is released as a void water. Thus, the height of the unsaturated and swollen gel whose void space is completely filled with liquid is increased from 0 cm and residual void liquid amounts of the gel layer are measured at respective predetermined heights, thereby calculating a distribution of void radiuses (capillary radiuses) of the swollen gel.

Hereinafter, in the present invention, a value indicative of the sample capillary radius R calculated at each height h by using the expression "$h = 2\gamma \cos \theta / \rho g R$" is defined as a void radius. A difference between a liquid surface height in the liquid tank and an intermediate position of the thickness of the glass filter is gradually increased from 0 to 60 (cm) by 1 cm, 2 cm, 5 cm, 8 cm, 10 cm, 15 cm, 20 cm, 25 cm, 30 cm, 40 cm, 50 cm, and 60 cm. This allows liquid retained in each void having an R value corresponding to each height to be removed. By measuring an amount of the removed liquid, it is possible to calculate a distribution of the sample void radiuses (capillary radiuses). Values thereof are plotted on a logarithmic probability paper, and a value indicative of d50 is regarded as a void average radius. The present embodiment adopts the expression "h=2γ cos θ/ρgR" where γ represents a surface tension (0.0728 N/m) of physiological saline water (0.9 wt % NaCl aqueous solution), θ represents a contact angle (0°), ρ represents a density (1000 kg/m$^3$) of the physiological saline water, g represents a gravitational constant (9.8 m/s$^2$).

The calculation shows that: liquid at the height of 0 cm is retained by a void whose void radius (capillary radius) is 1485 μm, liquid at the height of 1 cm is retained by a void whose void radius is 743 μm, liquid at the height of 2 cm is retained by a void whose void radius is 297 μm, liquid at the height of 5 cm is retained by a void whose void radius is 186 μm, liquid at the height of 8 cm is retained by a void whose void radius is 149 μm, liquid at the height of 10 cm is retained by a void whose void radius is 99.0 μm, liquid at the height of 15 cm is retained by a void whose void radius is 74.3 μm, liquid at the height of 20 cm is retained by a void whose void radius is 59.4 μm, liquid at the height of 25 cm is retained by a void whose void radius is 49.5 μm, liquid at the height of 30 cm is retained by a void whose void radius is 37.1 μm, liquid at the height of 40 cm is retained by a void whose void radius is 29.7 μm, and liquid at the height of 50 cm is retained by a void whose void radius is 24.8 μm. Note that, the measurement in the present invention is carried out under such condition that the target sample sufficiently absorbs liquid or is wet, so that θ is 0°.

(Production Method of the Water Absorbing Agent)

The method of the present invention for producing the water absorbing agent is not particularly limited as long as properties of the present invention are satisfied. However, the water absorbing agent of the present invention can be obtained in accordance with the following <Production Method 1> and <Production Method 2> for example.

<Production Method 1 (Aqueous Solution Polymerization)>

In case of adopting aqueous solution polymerization, an unsaturated monomer aqueous solution is cross-linked and polymerized in the presence of an internal cross-linking agent in a specific range, and the resultant hydrogel is crushed and dried, and the resultant is subjected to a granulation step so as to be specific water absorbent resin particles, and then the water absorbent resin particles are subjected to a treatment for enhancing a pressurized void average radius. That is, the aqueous solution polymerization may be arranged in any manner as long as the surface cross-linking agent and the agent for enhancing the pressurized void average radius index are used and a particle diameter and a bulk specific gravity are controlled and then the absorbency is adjusted to a below-described absorbency against pressure.

<Production Method 2 (Reversed Phase Suspension Polymerization)>

In case of adopting reversed phase suspension polymerization, an unsaturated monomer aqueous solution is cross-linked and polymerized in a hydrophobic organic solvent in the presence of an internal cross-linking agent in a specific range, and the resultant hydrogel is dried, and the dried hydrogel is subjected to a granulation step, as necessary, so as to be specific water absorbent resin particles, and then the water absorbent resin particles are subjected to a treatment for enhancing a pressurized void average radius index. That is, the reversed phase suspension polymerization may be arranged in any manner as long as the surface cross-linking agent and the agent for enhancing the pressurized void average radius index are used and a particle diameter and a bulk specific gravity are controlled and then the absorbency is adjusted to a below-described absorbency against pressure.

In these production methods, it is preferable to carry out a surface cross-linking treatment with respect to a surface of the water absorbent resin particles after the drying treatment.

The following describes (i) the method of the present invention for producing the water absorbing agent and (ii) the water absorbing agent of the present invention. Note that, unless either the Production Method 1 (aqueous solution polymerization) or the Production Method 2 (reversed phase suspension polymerization) is particularly specified in the beginning of each paragraph, each material can be used in both the methods.

(Monomer)

Examples of the water-soluble ethylenic unsaturated monomer include water-soluble monomer with carboxyl group, water-soluble monomer with sulfonic group, water-soluble monomer with amide group, and the like. It is preferable to use the water-soluble monomer with carboxyl group, and it is particularly preferable to use acrylic acid and/or salt thereof.

As the water absorbent resin particles usable in the present invention, it is preferable to use water absorbent resin particles made of polyacrylic acid (salt) cross-linked polymer obtained by polymerizing a monomer containing acrylic acid and/or salt thereof.

In the present invention, the polyacrylic acid (salt) cross-linked polymer is obtained by polymerizing a monomer containing preferably 50 to 100 mol %, more preferably 70 to 100 mol %, still more preferably 90 to 100 mol % of acrylic acid and/or salt thereof and internally includes a cross-linked structure. Further, preferably 25 to 100 mol %, more preferably 50 to 99 mol %, still more preferably 55 to 80 mol % of acid group in the polymer is neutralized. Examples of salt are one type of or two or more type of: alkali metal salt such as sodium, potassium, and lithium; ammonium salt; amine salt; and the like. The acid group for forming salt may be neutralized in a monomer phase before the polymerization or in a polymer phase during or after the polymerization, or the neutralization may be carried out in both the phases.

As to the polyacrylic acid (salt) cross-linked polymer favorably used in the present invention as the water absorbent resin particles, not only the water-soluble ethylenic unsaturated monomer (acrylic acid and/or salt thereof) used as a main component but also other monomer may be copolymerized as necessary.

The state in which "as a main component" a water-soluble ethylenic unsaturated monomer (acrylic acid and/or salt thereof) is included is such that an amount of the water-soluble ethylenic unsaturated monomer included in the unsaturated monomer aqueous solution is 70% or more, preferably 80% or more, with respect to the whole monomer.

Specific examples of other monomer are monomers exemplified in U.S. patents or European Patents which will be mentioned later concerning the polymerization method. Specific examples thereof include monomers each of which is copolymerized with water-soluble or hydrophobic unsaturated monomer and the like, e.g., (meth)acrylic acid, maleic (anhydride), fumaric acid, crotonic acid, itaconic acid, vinyl sulfonic acid, 2-(meth)acrylamide-2-methylpropane sulfonic acid, (meth)acryloxyalcane sulfonic acid and alkali metal salt thereof, ammonium salt, N-vinyl-2-pyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethyleneglycol(meth)acrylate, polyethyleneglycol(meth)acrylate, isobutylene, lauryl(meth)acrylate, and the like. An amount of the monomer other than the acrylic acid and/or salt thereof is preferably 0 to 30 mol %, more preferably 0 to 10 mol %, with respect to the whole monomer.
(Cross-Linked Structure)

The water absorbent resin particles usable in the present invention internally include a cross-linked structure.

As to a method for introducing the internal cross-linked structure into the water absorbent resin particles used in the present invention, examples thereof include: a method in which self-cross-linking is carried out without using any cross-linking agent so as to introduce the internal cross-linked structure; a method in which an internal cross-linking agent having two or more polymerizable unsaturated groups in its single molecule and/or two or more reactive groups in its single molecule is copolymerized or reacted so as to introduce the internal cross-linked structure; and a similar method.

Specific examples of the internal cross-linking agent include: copolymerizable cross-linking agents such as N,N'-methylenebis(meth)acrylamide, (poly)ethyleneglycol di(meth)acrylate, (poly)propyleneglycol di(meth)acrylate, trimethylolpropanetri(meth)acrylate, trimethylolpropanedi(meth)acrylate, glycerineacrylatemethacrylate, ethyleneoxide denatured trimethylolpropanetri(meth)acrylate, pentaerythritoltetra(meth)acrylate, dipentaerythritolhexa(meth)acrylate, triallyl cyanurate, triallyl isocyanurate, triallyl phosphate, triallyl amine, tetraallyloxyethane, pentaerythritoltriallylether, and poly(meth)allyloxyalcane; internal cross-linking agents, each of which has a copolymerizable group and a covalent binding group, e.g., (poly)ethyleneglycoldiglycidylether, glyceroldiglycidylether, ethylenediamine, polyethyleneimine, glycidyl(meth)acrylate, hydroxyethyl(meth)acrylate, hydroxypropyl(meth)acrylate, glycidyl(meth)acrylate, and the like.

Besides, examples of the internal cross-linking agent having two or more covalent binding groups or an ionic binding group include: polyhydric alcohol compounds such as ethyleneglycol, diethyleneglycol, propyleneglycol, triethyleneglycol, tetraethyleneglycol, polyethyleneglycol, 1,3-propanediol, dipropyleneglycol, 2,2,4-trimethyl-1,3-pentandiol, polypropyleneglycol, glycerin, polyglycerin, 2-butene-1,4-diol, 1,3-butandiol, 1,4-butandiol, 1,5-pentandiol, 1,6-hexanediol, 1,2-cyclohexanedimethanol, 1,2-cyclohexanol, trimethylolpropane, diethanolamine, triethanolamine, polyoxypropylene, oxyethlene-oxypropylene block copolymer, pentaerythritol, and sorbitol; multivalent metal compounds such as hydroxides or chlorides, e.g., zinc, calcium, magnesium, aluminum, iron, and zirconium; and the like.

These internal cross-linking agent may be used independently or in a combination of two or more kinds. In view of absorbent properties of the resultant water absorbent resin, it is preferable to essentially use a compound having two or more polymerizable unsaturated groups as the internal cross-linking agent in accordance with the method described in Tokugan 2005-289399 (International Publication No. 2007/03745 Pamphlet). Further, it is preferable that (i) the internal cross-linking agent having a copolymerizable group and a covalent binding group and (ii) the internal cross-linking agent having two or more covalent binding groups or an ionic binding group are used together. Particularly, it is preferable to use polyhydric alcohol together.

An amount of the internal cross-linking agent included in the water absorbent resin particles usable in the present invention is preferably 0.005 to 3 mol %, more preferably 0.01 to 2 mol %, still more preferably 0.2 to 2 mol %, particularly preferably 0.4 to 1.5 mol %, with respect to the whole monomer (water-soluble ethylenic monomer other than the internal cross-linking agent).

Further, in case of using, as the internal cross-linking agent of the present invention, (i) the internal cross-linking agent having two or more polymerizable unsaturated groups and (ii) the internal cross-linking agent having a copolymerizable group and a covalent binding group or the internal cross-linking agent having an ionic binding group together, an amount of the internal cross-linking agent (i) is preferably 0.005 to 3 mol % and an amount of the internal cross-linking agent (ii) is preferably 0 to 2.995 mol %, more preferably the amount of the internal cross-linking agent (i) is 0.01 to 2 mol % and the amount of the internal cross-linking agent (ii) is 0 to 1.99 mol %, particularly preferably the amount of the internal cross-linking agent (i) is 0.2 to 2 mol % and the amount of the internal cross-linking agent (ii) is 0 to 1.9 mol %, with respect to the whole monomer (water-soluble ethilenic monomer other than the internal cross-linking agent).

In carrying out the polymerization, it is possible to add hydrophilic polymers such starch or cellulose, a derivative of starch or cellulose, polyvinyl alcohol, polyacrylic acid (salt), cross-linked polyacrylic acid (salt), and the like so that an amount thereof is 0 to 30 wt % with respect to the whole monomer (water-soluble monomer other than the internal cross-linking agent), or it is possible to add a chain transfer agent such as hypophosphorous acid (salt) so that an amount thereof is 0 to 1 wt % with respect to the whole monomer (water-soluble monomer other than the internal cross-linking agent).

In case of using the water absorbent resin obtained by incorporating not only the unsaturated monomer, the internal cross-linking agent, and the polymerization initiator, but also a water-soluble chain transfer agent and carrying out polymerization, it is possible to obtain an absorbent core whose absorbing performance is high and whose stability with respect to urine is excellent.

The water-soluble chain transfer agent used to carry out polymerization in the present invention is not particularly limited as long as the chain transfer agent is dissolved in water or water-soluble ethylenic unsaturated monomer, and examples thereof include thiols, thiolic acids, secondary alcohols, amines, hypophosphites, and the like. Specific examples thereof include mercaptoethanol, mercaptopropanol, dodecylmercaptan, thioglycols, thiomalic acid, 3-mercaptopropionic acid, isopropanol, sodium hypophosphite, formic acid, and salts thereof. One kind or two or more kinds selected from them are used, but it is preferable to use hypophosphite such as sodium hypophosphite due to its effect. An amount of the water-soluble chain transfer agent depends on a type and an amount of the chain transfer agent and a concentration of the monomer aqueous solution, but ranges from 0.001 to 1 mol %, preferably from 0.005 to 0.3 mol %, with respect to the whole monomer.
(Polymerization Method)

In polymerizing the water-soluble ethylenic unsaturated monomer, preferably, acrylic acid and/or salt thereof as a main component so as to obtain the water absorbent resin particles usable in the present invention, it is preferable to carry out bulk polymerization, reversed phase suspension polymerization, or precipitation polymerization. However, in terms of (i) performance of the water absorbent resin particles and (ii) controllability of polymerization, a more preferable method of polymerization is aqueous solution polymerization or reversed phase suspension polymerization performed under such condition that an aqueous solution of the monomer is used. In the Production Method 1 of the present invention, the aqueous solution polymerization is adopted. In the Production Method 2 of the present invention, the reversed phase suspension polymerization is adopted.

Such polymerization method is recited for example in U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,683,274, U.S. Pat. No. 4,690,996, U.S. Pat. No. 4,721,647, U.S. Pat. No. 4,738,867, U.S. Pat. No. 4,748,076, European Patent No. 1178059.
(Polymerization Initiator)

In initiating the polymerization, it is possible to use: a radical polymerization initiator such as potassium persulfate, ammonium persulfate, sodium persulfate, t-butylhydroperoxide, hydrogen peroxide, 2,2'-azobis (2-amidino-propane) dihydrochloride; or an active energy ray such as an ultraviolet ray and an electron ray. Further, in case of using a radical polymerization initiator, redox polymerization may be carried out by using a reducer such as sodium sulfite, sodium bisulfite, ferrous sulfate, L-ascorbic acid, and the like, together. An amount of polymerization initiators used is preferably 0.001 to 2 mol %, more preferably 0.01 to 0.5 mol %, with respect to the whole monomer.

In carrying out the polymerization, the monomer aqueous solution may be in such a slurry state that its monomer concentration exceeds the saturated concentration, but it is preferable that the monomer concentration of the monomer aqueous solution is 35 wt % or more and is equal to or less than the saturated concentration, and it is more preferable that the monomer concentration is 37 wt % or more and is equal to or less than the saturated concentration. A temperature of the monomer aqueous solution preferably ranges from 0 to 100° C., more preferably from 10 to 95° C. Note that, the saturated concentration is defined by the temperature of the monomer aqueous solution.

Further, the water absorbent resin particles usable in the present invention may partially include foam particles. The foam particles are obtained by carrying out polymerization with an azo initiator and a foaming agent such as carbonate or by carrying out reversed phase suspension polymerization with O/W/O (oil/water/oil) or by carrying out polymerization with bubbles while bubbling inert gas.

A cross-linked polymer obtained by the foregoing polymerization is a hydrogel, and its shape is generally an irregularly-pulverized shape, a spherical shape, a bar shape, a fibrous shape, a rod shape, a substantially spherical shape, an oblate shape, and the like.

The following describes the reversed phase suspension polymerization of the Production Method 2 and gel crushing of the Production Method 1.
(Reversed Phase Suspension Polymerization of Production Method 2)

According to the Production Method 2 (reversed phase suspension polymerization), in polymerizing the aforementioned monomer for obtaining the water absorbing agent of the present invention, there is adopted the reversed phase suspension polymerization in which the monomer aqueous solution is dispersed in an inactively-polymerizable hydrophobic organic solvent in the presence of a dispersing agent. The polymerization method is described in U.S. Pat. No. 4,093,776, U.S. Pat. No. 4,340,706, U.S. Pat. No. 4,367,323, U.S. Pat. No. 4,446,261, U.S. Pat. No. 4,683,274, U.S. Pat. No. 4,880,888, U.S. Pat. No. 5,180,798, U.S. Pat. No. 5,244,735, U.S. Pat. No. 6,573,330, U.S. Patent Application No. 2007-015887, U.S. Patent Application No. 2006-194055, and the like. Also monomers and initiators that are exemplified in the aforementioned polymerization method are usable in the present invention.

The reversed phase suspension polymerization is a polymerization method in which a monomer is dispersed so that a polymerizable monomer aqueous solution is suspended or emulsified in a hydrophobic organic solvent. Examples of the surfactant (U.S. Pat. No. 6,458,896 and U.S. Pat. No. 6,107,358) or the dispersing agent for dispersing the monomer include an anionic surfactant, a nonionic surfactant, a cationic surfactant, an amopholytic surfactant, and the like.

Specific examples of the anionic surfactant include: fatty acid sodium such as mixed fatty acid sodium soap and sodium stearate; higher alcohol sodium sulfate; alkyl sodium sulfate; alkylbenzenesulfonic acid salt; alkylmethyltaurinate; polyoxyethylenealkylphenylether sulfate ester salt; polyoxyethylenealkylether sulfonic acid salt; sulfosuccinate half ester of alkylalcohol; and the like. Specific examples of the nonionic surfactant include: polyoxyethylenealkylether such as polyoxyethylene higher alcohol ether; polyoxyethylenealkylphenylether; sorbitan fatty acid ester; glycerine fatty acid ester; saccharose fatty acid ester; sorbitol fatty acid ester hexaglycerylmonobeherate; polyalkylenealkylphenylether phosphate ester; polyoxyalkylenealkylether phosphate ester; polyoxyalkylenealkylphenylether phosphate ester; polypxyalkylenearyl ether phosphate ester; and the like. Specific examples of the cationic surfactant and the amopholytic surfactant include: alkylamines, alkylbetaines, and the like. Further, examples of other dispersing agent include ethylcellulose, ethylhydroxyethylcellulose, polyethyleneoxide, polyethylene-polyacrylic acid copolymer, maleic anhydride polyethylene, maleic anhydride polybutadien, maleic anhydride EPDM (ethylene-propylene-dien-methylene copolymer), maleic anhydride polypropylene, and the like. These nonionic surfactants may be used independently or a mixture of two or more kinds may be used.

Out of these surfactants, there is used a nonionic surfactant or an anionic surfactant whose HLB (Hydrophile-Lipophile balance) is preferably 2 or more, more preferably 3 or more. For example, phosphate ester surfactant such as sorbitan fatty acid ester, saccharose fatty acid ester, ether nonionic surfactant is used. Note that, an upper limit of HLB is about 16.

An amount of the surfactant or the dispersing agent is suitably set depending on a type of the polymerization. Generally, the amount preferably ranges from 0.1 to 30 parts by mass, more preferably from 0.3 to 5 parts by mass, with respect to 100 parts by mass of the whole monomer constituted of the polymerizable monomer and the cross-linked monomer. Further, the amount of the surfactant or the dispersing agent ranges from 0.001 to 10 mass %, preferably from 0.001 to 1 mass %, with respect to a below-described organic solvent.

Any solvent can be used as an organic solvent used to carry out reversed phase suspension polymerization as long as the solvent is hardly dissolved in water and is inactive in polymerization. Examples thereof include: aliphatic hydrocarbons such as n-pentane, n-hexane, n-heptane, and n-octane; alicyclic hydrocarbons such as cyclohexane, and methylcyclohexane; aromatic hydrocarbons such as benzene, toluene, and xylene; and the like. Above all, it is preferable to use n-hexane, n-heptane, and cyclohexane, in view of (i) stability in industrially obtaining these solvents, (ii) quality, (iii) and the like. With respect to 1 part by mass of an aqueous solution containing polymerizable monomer, an amount of the hydrophobic solvent ranges from 0.5 to 10 parts by mass, preferably from 0.6 to 5 parts by mass.

In case of producing the water absorbent resin by carrying out the reversed phase suspension polymerization, an organic solvent such as n-hexane, n-heptane, cyclohexane is used to carry out the polymerization and then the surface cross-linking, the drying and granulation are carried out as described above. This raises such a problem that a minute amount of organic solvent exists in a conventional production method or in a commercial product and the like. The water absorbing agent of the present invention can be obtained also by the production method according to the present embodiment which includes the rinsing step.

In order to reduce the residual organic solvent, there is adopted a method in which the hydrogel obtained in the foregoing manner was rinsed with an organic solvent or inorganic solvent having a lower boiling point. As the organic solvent having a lower boiling point, it is preferable to use an organic solvent whose boiling point is 0° C. or higher and less than 70° C., further, 30° C. or higher and less than 50° C. Above all, it is preferable to use acetone, dimethylether, methylene chloride, and the like. Specifically, the hydrogel is filtered and then the filtered hydrogel is rinsed with the organic solvent having a lower boiling point, and the rinsed hydrogel is dried by hot air or in a similar manner. The rinse may be carried out after carrying out the drying treatment. It may be so arranged that: the organic solvent is removed at the time of a below-described surface cross-linking treatment carried out by high-temperature heating without carrying out the rinse or together with the rinse (first production method: heating treatment). An amount of the solvent used to rinse the water absorbent resin generally ranges from 0.5 to 100 parts by mass, preferably from 1 to 10 parts by mass, more preferably from 2 to 5 parts by mass, with respect to 1 part by mass of the water absorbent resin, and its temperature ranges from the room temperature to the boiling point.

(Gel Crushing of Production Method 1)

In the Production Method 1 (aqueous solution polymerization), the resultant hydrogel may be dried without any modification, but the hydrogel is extruded from a porous structure whose hole diameter is 0.3 to 6.4 mm so as to be crushed. A shape of the hole is a cyclic shape, a tetragonal shape such as square and rectangular, a triangle shape, or a hexagonal shape, and is not particularly limited, but the shape is preferably a cyclic shape. Note that, the hole diameter can be defined by a diameter in case where an external periphery of a mesh is converted into an external periphery of a circle.

The hole diameter of the porous structure for extruding the hydrogel so as to obtain crushed gel particles is more preferably 0.5 to 4.0 mm, more preferably 0.5 to 3.0 mm.

If the hole diameter of the porous structure is less than 0.3 mm, the gel may be in a string manner or the gel may be unable to be extruded. If the hole diameter of the porous structure is more than 6.4 mm, it may be impossible to exhibit the effect of the present invention.

An example of a device for extruding the hydrogel so as to obtain crushed gel particles is a device arranged so that the hydrogel polymer is extruded from a porous plate so as to crush the hydrogel polymer. Further, examples of an extruding mechanism include: a screw type, a rotary type, and the like; and a type in which the hydrogel polymer is carried with pressure from its feed opening to its porous plate. The screw type extruder may be monoaxial or polyaxial. Generally, it is possible to use an extruder used to extrude and mold meat, rubber, and plastic, or it is possible to use an extruder used as a crusher. Examples thereof are a meat chopper and a dome gran.

As described above, the monomer aqueous solution which contains a specific amount of internal cross-linking agent and which has a specific concentration is polymerized, and the resultant hydrogel is extruded under a specific condition, i.e., the hydrogel is extruded from the porous structure whose hole diameter is 0.3 to 6.4 mm, thereby crushing the hydrogel. In this case, water, polyhydric alcohol exemplified as the internal cross-linking agent, a mixture solution of water and polyhydric alcohol, a solution obtained by dissolving multivalent metal exemplified as the internal cross-linking agent or vapor thereof may be added to water.

After being subjected to the step in which the hydrogel obtained by the polymerization in the Production Method 1 is extruded from the porous structure whose hole diameter is preferably 0.3 to 6.4 mm so as to be crushed as crushed gel particles in the foregoing manner, the hydrogel is preferably dried. It is preferable to further pulverize the hydrogel after drying the hydrogel.

The common steps of the Production Methods 1 and 2 are described again as follows.

(Drying and Pulverizing)

A condition under which the hydrogel or the crushed hydrogel particles are dried is not particularly limited, but it is preferable that the temperature ranges from 80 to 250° C. and a drying time ranges from 10 to 180 minutes, and it is more preferable that the temperature ranges from 150 to 200° C. and the drying time ranges from 30 to 120 minutes. As an example of the drying method, it is possible to adopt various methods such as: a method in which azeotropic dehydration is carried out in the hydrophobic organic solvent used for the polymerization; and a high humidity drying method in which the hydrogel is filtered and then a general forced-draft oven, a reduced-pressure dryer, a microwave dryer, and high temperature vapor are used, so as to obtain a desired moisture content. In this manner, the drying method is not particularly limited. In the Production Method 2, it is preferable to carry out the azeotropic dehydration. Further, in the Production Method 2, the resultant is heated at 100° C. or higher after the azeotropic dehydration, thereby adjusting its moisture content to a desired value.

A moisture content (defined by a water content in the water absorbent resin/measurement was carried out with a drying loss at 180° C. for three hours) of the water absorbent resin or the water absorbing agent used in the present invention is not particularly limited. However, in view of properties, the resultant water absorbing agent is powder having fluidity also at a room temperature, so that its powdery state is such that the moisture content more preferably ranges from 0.1 to 30 mass %, 0.2 to 30 mass %, still more preferably from 0.3 to 15 mass %, particularly preferably from 0.5 to 10 mass %.

Due to the drying, a solid content (defined in Examples) of the hydrogel or the crushed hydrogel particles preferably ranges from 70 to 99.8 wt %, more preferably from 80 to 99.7 wt %, more preferably from 90 to 99.5 wt %. If the solid content deviates from this range, it is difficult to obtain the water absorbing agent of the present invention.

A condition under which the hydrogel or the crushed hydrogel particles are pulverized preferably after being dried is not particularly limited, but it is possible to use a conventionally known pulverizer such as a roll mill, a hummer mill, and the like.

A shape obtained by the pulverization in the Production Method 1 is an irregularly-pulverized shape. It is preferable to pulverize the dried hydrogel into a substantially spherical shape. Further, preferable shapes are a spherical shape and a substantially spherical shape which are obtained by the reversed phase suspension polymerization in the Production Method 2 without carrying out pulverization.

Note that, as described in Japanese Unexamined Patent Publication No. 11106/2001 (Tokukai 2001-11106), reversed phase suspension polymerization is carried out at two stages, thereby greatly controlling the particle diameter. Further, as described in International Publication No. 2004/083284 Pamphlet, the water absorbent resin may be post-cross-linked with a post-cross-linking agent after a final-stage reversed phase suspension polymerization, and the resultant may be an agglomerate or may be free from any agglomerate of particles. However, it is preferable that the resultant is an agglomerate. The greater the particle size is and the larger the amount of the internal cross-linking agent is, the more preferable.

(Granulation)

The water absorbent resin particles usable in the present invention may partially include granulated particles. The granulated particles are obtained by granulating particles whose particle diameter is less than 150 μm. A method for partially granulating the water absorbent resin particles is not particularly limited, and a conventionally known granulation method is adopted.

Examples of the granulation method include: a method in which hot water and fine powder of the water absorbent resin particles are mixed with each other and thus obtained mixture is dried (U.S. Pat. No. 6,228,930); a method in which fine powder of the water absorbent resin particles is mixed with a monomer aqueous solution and thus obtained mixture is polymerized (U.S. Pat. No. 5,264,495); a method in which water is added to fine powder of the water absorbent resin particles and thus obtained mixture is granulated at not less than a specific surface pressure (European Patent No. 844270); a method in which fine powder of the water absorbent resin particles is sufficiently swollen so as to form a non-crystalline gel and thus obtained non-crystalline gel is dried and crushed (U.S. Pat. No. 4,950,692); a method in which fine powder of the water absorbent resin particles is mixed with a polymerized gel (U.S. Pat. No. 5,478,879); a method in which agglomeration is carried out by reversed phase suspension polymerization (U.S. Pat. No. 4,732,968); and a similar method.

(Particle Diameter)

The water absorbent resin particles usable in the present invention are further classified or granulated for example, thereby adjusting its mass average particle diameter (D50) to preferably 150 to 500 μm, more preferably 200 to 450 μm, still more preferably 250 to 400 μm. Further, its logarithmic standard deviation (σζ) is adjusted to preferably 0.25 to 0.45, more preferably 0.25 to 0.40, still more preferably 0.25 to 0.35. As to the water absorbent resin particles usable in the present invention, the mass average particle diameter and the logarithmic standard deviation (σζ) are adjusted in this manner, thereby further exhibiting the effect of the present invention.

In the present invention, it is necessary to select a sieve, used in the classification carried out as necessary, with a classification efficiency taken into consideration. For example, in case where water absorbent resin particles or water absorbing agent having passed through a sieve whose mesh size is 150 μm are removed by carrying out the classification operation, it is difficult to completely remove particles whose particle diameter is 150 μm or less. Thus, in order to obtain water absorbent resin particles or water absorbing agent having a desired particle diameter, it is preferable to suitably select a type of the sieve to be used.

In order to further exhibit the effect of the present invention, the water absorbent resin particles usable in the present invention include preferably 90 to 100 wt %, more preferably 95 to 100 wt %, still more preferably 98 to 100 wt %, particularly preferably 99 to 100 wt % of particles whose particle diameter is 150 to 850 μm. Further, the water absorbent resin particles include still more preferably 90 to 100 wt %, particularly preferably 95 to 100 wt % of particles whose particle diameter is 150 to 600 μm. If an amount of particles whose particle diameter is less than 150 μm is large, it may be impossible to sufficiently exhibit the effect of the present invention.

Further, in order to further exhibit the effect of the present invention, an amount (defined by sieve classification) of water absorbent resin particles whose particle diameter is 300 μm or more and 600 μm or less is preferably 20 to 90 mass %, more preferably 50 to 80 mass %, with respect to the entire amount of the water absorbent resin particles.

In order to obtain the water absorbing agent of the present invention, a bulk specific gravity (defined in U.S. Pat. No. 6,562,879) of the water absorbent resin particles in the present invention preferably ranges from 0.72 to 1.00 g/ml, more preferably from 0.74 to 0.88 g/ml, still more preferably from 0.76 to 0.86 g/ml. In case where the bulk specific gravity deviates from this range, it may be difficult to exhibit the effect of the present invention.

The particle diameter and the bulk specific gravity are obtained, for example, by carrying out reversed phase suspension polymerization with a specific surfactant or by drying/pulverizing the resultant having been subjected to aqueous solution polymerization and grinding a surface of the resultant particles. Note that, each of U.S. Pat. No. 5,998,553, U.S. Pat. No. 6,562,879, and U.S. Pat. No. 6,576,713 discloses a surface-cross-linked water absorbent resin whose bulk specific gravity is 0.72 or more, but the agent for enhancing the pressurized void average radius index is not added, or the absorbency against pressure is low, which does not allow the pressurized void average radius of the present invention to be satisfied.

Further, also a water absorbing agent whose surface is cross-linked after the reversed phase suspension polymerization is known (see U.S. Pat. No. 4,507,438 and U.S. Pat. No. 4,541,871), but the agent for enhancing the pressurized void average radius index is not added, or the absorbency against pressure is low, which does not allow the pressurized void average radius of the present invention to be satisfied.

Further, each of Patent Document 4 and 5 discloses the water absorbent resin whose inter-particle void average radius is controlled. However, according to the technique disclosed by these documents (control of an average particle diameter, addition of cation polymer or inorganic fine particles, etc., and Referential Examples 1 to 6), it is extremely difficult or impossible to enhance the pressurized void average radius index according to the present invention. The inventors of the present invention achieved values exceeding property values disclosed by Patent Documents 4 and 5 by adopting a technique which is not disclosed by the documents, and they found that the novel water absorbing agent is effective in a highly-concentrated diaper.

The agent for enhancing the pressurized void average radius index is described as follows.

(Treatment for Enhancing Pressurized Void Average Radius Index)

In order to obtain the water absorbing agent of the present invention, it is necessary to carry out the treatment for enhancing the pressurized void average radius index.

The treatment for enhancing the pressurized void average radius index is not particularly limited, but it is preferable to add an agent for enhancing the pressurized void average radius index. That is, it is preferable that the water absorbing agent of the present invention includes the agent for enhancing the pressurized void average radius index.

In the present invention, in case of carrying out a below-described surface treatment (cross-linking) with respect to the water absorbent resin particles, the treatment (step) for enhancing the pressurized void average radius index may be carried out before, at the same time as, or after the surface treatment. However, in order to further exhibit the effect of the present invention, it is preferable to carry out the treatment for enhancing the pressurized void average radius after the surface treatment (cross-linking) and separately from the surface treatment (cross-linking).

As the agent for enhancing the pressurized void average radius index, it is possible to use a compound selected from a multivalent metal compound, inorganic fine particles, and polycation polymer compound, further, a compound selected from water-soluble multivalent metal salt, water-insoluble inorganic fine particles, and a polyamine polymer compound (weight average molecular weight is 1000 or more, further, ranges from 10000 to million). Out of inorganic agents for enhancing the pressurized void average radius index, the water-soluble multivalent metal salt is particularly preferable.

Examples of the agent for enhancing the pressurized void average radius include: multivalent metal compounds such as ammonium zirconium carbonate, aluminum sulfate, potassium alum, ammonium alum, sodium alum, aluminum (poly) chloride, and a hydrate thereof; polycation polymer compounds such as polyethyleneimine, polyvinylamine, and polyallylamine; water-insoluble inorganic fine particles such as silica, alumina, and bentonite; and the like. These agents may be used independently or in a suitable combination of two or more kinds. Above all, water-soluble multivalent metal salts (particularly, aluminum salt) such as aluminum sulfate and potassium alum are preferable in enhancing the pressurized void average radius index. It is preferable that the multivalent metal salt is any one of bivalent, trivalent, and tetravalent metal salts.

An amount of the agent for enhancing the pressurized void average radius index preferably ranges from 0.001 to 10 wt %, more preferably from 0.01 to 5 wt %, further from 0.05 to 3 wt %, particularly from 0.08 to 2 wt %, with respect to the water absorbent resin particles. Note that, in case where the multivalent metal salt is hydrate (e.g., aluminum sulfate hexadecahydrate), the amount includes a weight of water molecules. Further, the amount of the added agent depends on a particle diameter (superficial area) of the water absorbent resin particles. In case where a superficial area with respect to a volume of the water absorbent resin is large (in case where the particle diameter of the water absorbent resin is small), a large amount of the agent for enhancing the pressurized void average radius index is required. Adversely, in case where the superficial area with respect to the volume of the water absorbent resin is small (in case where the particle diameter of the water absorbent resin is large), a small amount of the agent is required. Further, the amount of the agent for enhancing the pressurized void average radius index depends also on a gel strength after the water absorbent resin particles absorb liquid. In case where the gel strength is high, a small amount of the agent is required. Adversely, in case where the gel strength is low, a large amount of the agent is required.

A method for adding the agent for enhancing the pressurized void average radius index is not particularly limited. The agent may be dry-blended, added as an aqueous solution, or may be thermally melted so as to be bonded.

More specifically, the "dry blend" is a process in which the agent for enhancing the pressurized void average radius index, e.g., solid and powdery multivalent metal compound or inorganic fine particles are evenly mixed with the dried and pulverized water absorbent resin particles. After the mixture, water and polyhydric alcohol aqueous solution may be added and mixed and the resultant may be further heated as necessary. The "addition of aqueous solution" is a process in which aqueous solution of multivalent metal compound or polycation compound is added and mixed with the water absorbent resin particles. It is more preferable that a concentration of the multivalent metal compound or the polycation compound is higher. Further, the resultant may be heated as necessary after the mixture. The "thermal melting" is a process in which: in or after mixing multivalent metal hydrate such as aluminum sulfate, potassium alum, ammonium alum, and sodium alum with the water absorbent resin particles, the multivalent metal compound is mixed with the water absorbent resin particles to be heated or the water absorbent resin particles having been heated beforehand, so as to melt the multivalent metal hydrate, thereby bonding the melted multivalent metal compound. As necessary, water may be added before heating.

(Surface Cross-Linking)

In order to further exhibit the effect of the present invention, it is preferable that a surface of the water absorbent resin particles usable in the present invention is cross-linked.

The step of cross-linking the surface of the water absorbent resin particles so as to obtain water absorbent resin particles is carried out preferably before, in, or after the step of carrying out the treatment for enhancing the pressurized void average radius.

As the surface cross-linking agent usable for the surface cross-linking treatment, it is possible to use an organic surface cross-linking agent, a multivalent metal compound, polycation, and the like, each of which has two or more functional groups reactive with functional group of the water absorbent resin particles, particularly, two or more functional groups reactive with carboxyl group. It is preferable to use them together. In obtaining the water absorbing agent of the present invention, the organic surface cross-linking agent is used out of the foregoing surface cross-linking agents. At this time, the aforementioned agents for enhancing the pressurized void average radius index (particularly, an organic agent for enhancing the pressurized void average radius index, further multivalent metal salt) are used solely or used together.

Examples thereof include: polyhydric alcohols such as ethyleneglycol, diethyleneglycol, propyleneglycol, triethyleneglycol, tetraethyleneglycol, polyethyleneglycol, 1,3-propanediol, dipropyleneglycol, 2,2,4-trimethyl-1,3-pentandiol, polypropyleneglycol, glycerin, polyglycerin, 2-butene-1,4-diol, 1,3-butandiol, 1,4-butandiol, 1,5-pentandiol, 1,6-hexanediol, 1,2-cyclohexanedimethanol, 1,2-cyclohexanol, trimethylolpropane, diethanolamine, triethanolamine, polyoxypropylene, oxyethlene-oxypropylene block copolymer, pentaerythritol, and sorbitol; epoxy compounds such as ethyleneglycol diglycidyl ether, polyethyleneglycol diglycidyl ether, glycerol polyglycidyl ether, diglycerol polyglycidyl ether, polyglycerol polyglycidyl ether, propyleneglycol diglycidyl ether, polypropyleneglycol diglycidyl ether, and glycidol; multivalent amine compounds such as ethylenediamine, diethylenetriamine, triethylenetetramine, tetraethylenepentamine, pentaethylenehexamine, and polyethyleneimine, and inorganic salts or organic salts thereof (for example, azetidinium salt and the like); multivalent isocyanate compounds such as 2,4-tolylenediisocyanate, and hexamethylenediisocyanate; multivalent oxazoline compounds such as 1,2-ethylenebisoxazoline; carbonic acid derivatives such as urea, thiourea, guanidine, dicyandiamide, and 2-oxazolidinon; alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 4-methyl-1,3-dioxane-2-one, 1,3-dioxane-2-one, and 4,6-dimethyl-1,3-dioxane-2-one; haloepoxy compounds such as epichlorohydrin, epibromohydrin, and α-methylepichlorohydrin, and multivalent amine addition products thereof (for example, Kymene produced by Hercules: registered trademark); silane coupling agents such as γ-glycidoxypropyltrimethoxysilane and γ-aminopropyltriethoxysilane; and oxethane compounds such as 3-methyl-3-oxethane methanol, 3-ethyl-3-oxethane methanol, 3-butyl-3-oxethane methanol, 3-methyl-3-oxethane ethanol, 3-ethyl-3-oxethane ethanol, 3-butyl-3-oxethane ethanol, 3-chloromethyl-3-methyloxethane, 3-chloromethyl-3-ethyloxethane, and a multivalent oxethane compound; multivalent metal compounds such as hydroxide or chloride, e.g., zinc, calcium, magnesium, aluminum, iron, and zirconium; and the like.

These surface cross-linking agents may be used either independently or in a suitable combination of two or more kinds. Among the cross-linking agents, the polyhydric alcohol is preferable since it is superior in terms of safety and it improves the hydrophilic property of the surface of the water absorbent resin particles. Further, the use of the polyhydric alcohol allows affinity between the surface of the water absorbent resin particles and a water-soluble multivalent metal salt to be improved, and a synergy effect between a polyhydric alcohol residue and a surface of the water-soluble multivalent metal salt enables the water-soluble multivalent metal salt to more evenly exist on the surface of the water absorbent resin particles.

An amount of the surface cross-linking agent used is preferably 0.001 to 5 parts by weight (parts by mass) with respect to 100 parts by weight of solid components of the water absorbent resin particles.

In mixing the surface cross-linking agent with the water absorbent resin particles, water may be used. An amount of water to be used is preferably over 0.5 parts by weight and not more than 10 parts by weight, more preferably 1 part by weight to 5 parts by weight, with respect to 100 parts by weight of solid components of the water absorbent resin particles.

In mixing the surface cross-linking agent and aqueous solution thereof, a hydrophilic organic solvent exemplified in U.S. Pat. No. 5,610,208 or a third substance may be used as a mixing auxiliary agent. An amount of the hydrophobic organic solvent depends on a type, a particle diameter, a moisture content, and the like of the water absorbent resin particles, but is preferably 10 parts by weight or less, more preferably ranges from 0.1 to 5 parts by weight with respect to 100 parts by weight of the solid components of the water absorbent resin particles. Further, inorganic acid, organic acid, polyamino acid, and the like which are mentioned as the third substance in U.S. Pat. No. 5,610,208 may exist. These mixing auxiliary agents may act as a surface cross-linking agent. However, it is preferable to use an agent which does not decrease the water absorbing performance of the water absorbent resin particles after carrying out the surface cross-linking treatment. Particularly, a volatile alcohol whose boiling point is less than 150° C. evaporates at the time of the surface cross-linking treatment, so that there is no residue. Thus, it is preferable to use such a volatile alcohol.

A method in which the water absorbent resin particles and the surface cross-linking agent are mixed with each other is not particularly limited, but the following mixing methods may be performed: the water absorbent resin particles are immersed in the hydrophilic organic solvent, and a surface cross-linking agent dissolved in water and/or the hydrophilic organic solvent as required is mixed; the surface cross-linking agent dissolved in the water and/or the hydrophilic solvent is sprayed or dropped directly to the water absorbent resin particles. Further, in case of spraying the surface cross-linking agent, a size of the sprayed droplet preferably ranges from 1 to 300 µm, more preferably from 2 to 200 µm.

After blending the water absorbent resin particles and the surface cross-linking agent, it is general to carry out a heating treatment preferably, thereby completing the cross-linking reaction. A temperature of the heating treatment depends on the surface cross-linking agent to be used, but is preferably 40° C. or higher and 250° C. or lower, more preferably 150° C. or higher and 250° C. or lower. In case where the treatment temperature is lower than 40° C., it may be impossible to sufficiently improve absorbent properties such as an absorbency against pressure. In case where the treatment temperature exceeds 250° C., this may result in deterioration of the water absorbent resin particles. As a result, the performance may be impaired. Thus, it is necessary to give sufficient attention to adjustment of the treatment temperature. A heating time preferably ranges from one minute to two hours, more preferably from 5 minutes to one hour. The surface cross-linking with a specific particle size is carried out so as to enhance the absorbency against pressure up to a predetermined range, thereby enhancing the pressurized void average radius index.

(Properties of Water Absorbing Agent)

The water absorbing agent provided in accordance with the above-exemplified production method is a novel water absorbing agent.

That is, the first water absorbing agent of the present invention is a novel water absorbing agent which essentially includes water absorbent resin particles obtained by polymerizing a water-soluble ethylenic unsaturated monomer and internally including a cross-linked structure, wherein a pressurized void average radius index is 140 or more.

Further, the second water absorbing agent of the present invention essentially includes water absorbent resin particles obtained by polymerizing a water-soluble ethylenic unsaturated monomer of the present invention and internally including a cross-linked structure, wherein 90 wt % or more of particles in the water absorbing agent is particles whose particle diameter ranges from 150 to 850 µm, and a pressurized void average radius index is 100 or more.

Further, the third water absorbing agent of the present invention essentially includes water absorbent resin particles which are obtained by polymerizing a water-soluble ethylenic unsaturated monomer and which internally include a cross-linked structure, wherein 90 wt % or more of the water absorbing agent obtained by reversed phase suspension polymerization is particles whose particle diameter ranges from 150 to 850 µm, and the water absorbing agent has a pressurized void average radius index. It is preferable that a surface of the water absorbing agent is cross-linked, and the water absorbing agent exhibits the aforementioned pressurized void average radius index and other properties. A shape of the water absorbing agent is spherical. Further, the water absorbing agent is preferably in a granulated manner. As to the third water absorbing agent, it is possible to favorably enhance the pressurized void average radius index while keeping other properties such as CRC and AAP.

The following describes properties of the water absorbing agent of the present invention.

(a) Pressurized Void Average Radius Index

The water absorbing agent of the present invention is characterized by a high pressurized void average radius index. The pressurized void average radius index is essentially 100 or more, preferably 120 or more, more preferably 140 or more, still more preferably 150 or more, further still more preferably 160 or more, further still much more preferably 170 or more, particularly preferably 200 or more, and most preferably 300 or more. An upper limit thereof is not particularly limited, but is preferably 1000 or less, more preferably 800 or less. In case where the upper limit is less than 140, for example, urine is hardly dispersed in the absorbent core, which may result in leakage. Further, in case where the upper limit exceeds 1000, the liquid is excessively well dispersed adversely, which may result in leakage.

Further, for the aforementioned reason, the pressurized void average radius index (logarithmic average standard deviation ($\sigma\zeta$)) of the water absorbing agent according to the present invention ranges from 0.2 to 1.5, preferably from 0.4 to 1.4.

(b) Shape

A shape of the water absorbing agent according to the present invention is not particularly limited as long as the properties are satisfied. However, examples of the shape are sheet shape, fibrous shape, and the like. It is particularly preferable that the shape is a particulate shape or a spherical shape. Further, in view of balance of properties, it is preferable that the water absorbing agent is in a granulated manner (e.g., granulated spherical particles).

In case where the water absorbing agent according to the present invention is particulate, a particle diameter and a particle diameter distribution of the water absorbing agent are not particularly limited. However, in order to further exhibit the effect of the present invention, a mass average particle diameter preferably ranges from 150 to 850 μm, more preferably from 200 to 600 μm, still more preferably from 250 to 500 μm. Further, a logarithmic standard deviation ($\sigma\zeta$) preferably ranges from 0.45 to 0.20, more preferably from 0.35 to 0.22, still more preferably from 0.30 to 0.25. Further, it is preferable that particles whose mass average particle diameter ranges from 300 to 600 μm are included. A ratio thereof (defined by sieve classification) preferably ranges from 20 to 90 wt %, more preferably from 50 to 80 wt %. Further, the bulk specific gravity ranges from 0.72 to 1.00 g/ml, more preferably from 0.74 to 0.88 g/ml, still more preferably from 0.76 to 0.86 g/ml. In case where the bulk specific gravity deviates from the foregoing range, it may be difficult to exhibit the effect of the present invention.

In case where the water absorbing agent according to the present invention is particulate, in order to further exhibit the effect of the present invention, the water absorbing agent includes preferably 90 to 100 wt %, more preferably 95 to 100 wt %, still more preferably 98 to 100 wt %, particularly preferably 99 to 100 wt % of particles whose particle diameter in a standard sieve ranges from 150 to 850 μm. In case where a large number of particles whose particle diameter is less than 150 μm is included, the liquid permeability deteriorates, so that it may be impossible to sufficiently exhibit the effect of the present invention. In case where a large number of particles whose particle diameter exceeds 850 μm, for example, gel particles having absorbed liquid greatly move in practical use, so that the absorbent core loses its original shape, which may result in urine leakage from a diaper or uncomfortable feeling for a human body.

(b) Centrifuge Retention Capacity (CRC)

In the water absorbing agent of the present invention, its centrifuge retention capacity (CRC) is 10 g/g, or more, more preferably 15 to 60 g/g, still more preferably 20 to 40 g/g or more, particularly preferably 25 to 35 g/g. If the centrifuge retention capacity (CRC) is less than 10 g/g, an amount of the water absorbing agent is larger, so that a diaper is thicker for example. If the centrifuge retention capacity (CRC) is more than 60 g/g, dispersion of absorbed liquid may be impaired.

(c) Absorbency Against Pressure (AAP)

An absorbency against pressure (AAP) of the water absorbing agent of the present invention preferably ranges from 10 to 30 g/g, more preferably from 15 to 30 g/g, still more preferably from 20 to 29 g/g, particularly preferably from 22 to 28 g/g where the pressure is 4.83 kPa. If the absorbency against pressure (AAP) is less than 10 g/g, the amount of the water absorbing agent is larger, so that a diaper is thicker for example.

(d) Difference Between the Absorbency Against Pressure (AAP) where the Pressure is 4.83 kPa and the Centrifuge Retention Capacity (CRC)

In the water absorbing agent of the present invention, the difference between the absorbency against pressure (AAP) where the pressure is 4.83 kPa and the centrifuge retention capacity (CRC) is 7 g/g or less, preferably 6 g/g or less, more preferably 5 g/g or less. In case where the difference between the absorbency against pressure (AAP) and the centrifuge retention capacity (CRC) exceeds 7 g/g, a liquid dispersing property under pressure may be impaired. A lower limit thereof may be minus (−3, further −1 for example), but is generally zero. The properties (a) to (d) can be realized by suitably adjusting the internal cross-linking and the surface cross-linking in accordance with the aforementioned technique.

(e) Free Swell Rate (FSR)

In the water absorbing agent of the present invention, a free swell rate (FSR) with respect to 20-fold physiological saline water is not less than 0.05 g/g/s, preferably not less than 0.1 g/g/s, more preferably not less than 0.2 g/g/s, still more preferably not less than 0.3 g/g/s, further still more preferably not less than 0.5 g/g/s, particularly preferably not less than 0.7 g/g/s. An upper limit thereof is not particularly limited but is preferably not more than 10 g/g/s, more preferably not more than 5 g/g/s. In case where the free swell rate (FSR) is smaller than 0.2 g/g/s, urine is not sufficiently absorbed and leaks on the occasion of the use in a diaper for example. The FSR can be improved by foaming or granulation.

(f) Extractable Content

In the water absorbing agent of the present invention, its extractable content preferably ranges from 0 to 15 wt %, more preferably from 0 to 10 wt %, still more preferably from 0 to 8 wt %. If the extractable content exceeds 15 wt %, this may cause a slimy condition on the occasion of the use in a diaper for example. The extractable content can be controlled by polymerization temperature, concentration, an amount of cross-linking agent, and the like.

(g) Component Other than the Water Absorbent Resin

The water absorbing agent according to the present invention includes the above-described water absorbent resin particles. In case where the water absorbing agent according to the present invention includes water absorbent resin particles which have not been subjected to the treatment for enhancing the pressurized void average radius index, it is preferable that the water absorbing agent further includes an agent for enhancing the pressurized void average radius index with the aforementioned content thereof. In case where the water absorbing agent according to the present invention includes water absorbent resin particles which have been subjected to the treatment for enhancing the pressurized void average radius index, only the water absorbent resin particles may be regarded as the water absorbing agent according to the present invention.

Further, the water absorbing agent according to the present invention may include a deodorant agent (exemplified in U.S. Pat. No. 6,469,080 for example), an antibacterial agent, a reducing agent (exemplified in U.S. Pat. No. 4,959,060 for example), a surfactant, an oxidation inhibitor, an oxidizer, and a chelating agent (exemplified in U.S. Pat. No. 6,599,989 for example) so that preferably 0 to 10 wt %, further, 0.001 to 5 wt %, 0.05 to 3 wt % of the aforementioned additive is added to the water absorbent resin particles. It is preferable that the surfactant is included with the aforementioned amount with respect to the water absorbing agent because it is possible to suppress impairment of properties at the time of transport or storage. Further, in view of a water absorbing rate and impact resistance, the water absorbing agent according to the present invention includes a predetermined amount of water, preferably 0.1 to 15 wt %, more preferably 0.5 to 10 wt %, particularly preferably 0.8 to 9 wt % of water. It is preferable to use the chelating agent and the reducing agent in view of urine-proof property and prevention of coloring.

(Purpose of Use)

The water absorbing agent according to the present invention is favorably used for a sanitary material of a diaper or the like, a water absorbing agent for a portable toilet, a waste liquid solidifying agent, an agricultural water retaining agent, and the like. The water absorbing agent according to the present invention is favorably used particularly for a sanitary material of a diaper or the like.

The absorbing article of the present invention absorbs feces or blood and includes: (a) the particulate water absorbing agent, (b) an absorbent core obtained by forming a hydrophilic fiber into a sheet shape as required, (c) a liquid permeable front sheet, and (d) a liquid impermeable back sheet. The absorbent core in case where the hydrophilic fiber is not used is arranged by fixing the water absorbing agent onto paper and/or nonwoven fabric. Further, in case where the particulate water absorbing agent is blended or sandwiched with a fiber material (pulp), the fiber material used is, for example, crushed wood pulp or a hydrophilic fiber such as a cotton linter, a cross-linked cellulose fiber, rayon, cotton, wool, acetate, or vinylon. These fiber materials are preferably aerated.

The absorbent core contains the particulate water absorbing agent at an amount (core concentration) of 30 to 100 mass %, preferably 40 to 100 mass %, more preferably 50 to 100 mass %, still more preferably 60 to 100 mass %, particularly preferably 70 to 100 mass %, most preferably 75 to 95 mass %, thereby exhibiting the effect of the present invention. For example, in case of using the particulate water absorbing agent with the aforementioned concentration, particularly in case of using the particulate water absorbing agent for an absorbent core top layer, high permeability (permeability potential under pressure) results in an excellent diffusion property with respect to absorbed liquid such as urine, so that it is possible to provide an absorbing article such as a disposable diaper whose absorption amount is increased due to efficient liquid distribution and whose absorbent core keeps its sanitary whiteness.

Further, it is preferable that the absorbent core is compression-molded to a density of 0.06 g/cc or more and 0.50 g/cc or less and a basic weight of 0.01 $g/cm^2$ or more and 0.20 $g/cm^2$ or less.

EXAMPLES

The following describes Examples and Comparative Examples so as to further detail the present invention, but the present invention is not limited to these Examples.

Properties of the water absorbing agent (or the water absorbent resin particles) were measured in accordance with the following method.

In the measurement, all the electric devices were used under such condition that each voltage thereof was 200V or 100V and each frequency thereof was 60 Hz. The measurement was carried out under such condition that a temperature was 25° C.±2° C. and a relative humidity was 50% RH. Further, 0.90 mass % sodium chloride aqueous solution was used as a physiological saline water. The following measurement method and reagents and measurement tools exemplified in Examples may be replaced with other corresponding items.

<(a) Pressurized Void Average Radius Index>

With a measurement device illustrated in FIG. 2, an unpressurized inter-gel void index of saturated and swollen water absorbing agent particles was measured in accordance with the following steps.

<<Step (1)>>

A conduit 203 was connected to a lower portion of a glass filter 202 whose surface absorbs liquid of a filter funnel 201 (glass filter particle No. #3: its thickness was 5 mm and its average particle diameter was 20 to 30 μm and its height was 60 cm, free from any air). Then, the other end of the conduit 203 was connected to an inlet provided on a lower portion of a liquid tank 204 whose diameter was 10 cm. At this time, sufficient adjustment had to be carried out so that no air remained in the glass filter 202. The filter funnel 201 was fixed with a clamp 205 so that the glass filter 202 was kept in a horizontal direction. The filter funnel 201 and its lower portion and the conduit 203 were filled with a physiological saline water (0.9 wt % sodium chloride aqueous solution) 206. The liquid tank 204 placed on a scale 207, and the scale 207 was connected to a computer 210 so that a change in a liquid mass in the liquid tank 204 was recorded by the computer 210.

As to the filter funnel 201 fixed with the clamp 205, an automatic elevator 208 allows the glass filter 202 to be automatically elevated to each height in accordance with a preset program. Note that, an elevation speed at this time was 1.0 cm/sec. It was confirmed that the conduit 203 and the lower portion of the glass filter 202 of the filter funnel 201 were free from any air, and then a liquid top surface level of the physiological saline water 206 of the liquid tank 204 and an intermediate position level of the thickness of the glass filter 202 were made identical to each other (height was 0 cm).

Next, the filter funnel 201 was raised so that a difference between the intermediate position level of the thickness of the glass filter 202 and the liquid top surface level of the physiological saline water 206 was 60 cm, and a value of the scale 207 was set to 0. Note that, on the basis of a position (height was 0) in which the liquid top surface level of the physiological saline water 206 of the liquid tank 204 and the intermediate position level of the thickness of the glass filter 202 were identical to each other, a height of the filter funnel 201 corresponded to a difference between the height of 0 cm and the intermediate position level of the thickness of the glass filter 202.

<<Step (2)>>

After the computer 210 had begun to record the liquid mass, a target sample 209 (water absorbing agent or water absorbent resin particles) was placed on the glass filter 202 under the following condition, and an acrylate resin piston 211 was placed on the target sample 209, and a weight 212 having in its center vertical through holes whose diameter was 15 mm was placed thereon. A total pressure of the piston 211 and the weight 212 was adjusted to 2.07 kPa. Note that, an external diameter of the piston 211 was slightly smaller than 60 mm, and there was little gap between the filter funnel 201 and an internal wall of the piston 211. Due to this arrangement, upward and downward movements thereof would not be hampered. Further, a height of the piston 211 was 3 cm, and had vertical through holes therein as illustrated in FIG. 3, and a stainless 400-mesh metal gauze was fused and bonded to a bottom of the piston 211.

(When the Target Sample 209 was Particulate)

0.900 g of water absorbing agent particles or 0.900 g (W) of water absorbing agent particles having been sieved so that a particle diameter thereof ranged from 600 to 300 μm were evenly dispersed on the glass filter 202 quickly.

(When the Target Sample 209 was not Particulate)

A sample was punched into a cyclic shape whose diameter was 57 mm, and a weight (W) of the sample under a dried condition was measured and then was placed on the glass filter 202.

Note that, the same measurement was carried out also under such condition that the target sample 209 was not placed on the glass filter 202, that is, under a blank condition.

<<Step (3)>>

The height difference from the height of the intermediate position level of the thickness of the glass filter 202 was set to be −3 cm (the glass filter 202 was positioned lower), and the sample was swollen until the change in the liquid mass became less than 0.005 g/min (for example, for 30 minutes). At this time, the sample was completely immersed in the physiological saline water and was made free from any air bubbles.

<<Step (4)>>

The height difference from the height of the intermediate position level of the thickness of the glass filter 202 was set to be 0 cm, and the glass filter 202 was kept at the same height until the change in the liquid mass became less than 0.005 g/min (for 60 minutes for example). At the time when the change in the liquid mass became less than 0.005 g/min, the value (g) of the scale was A0.

<<Step (5)>>

The height difference (cm) from the height of the intermediate position level of the thickness of the glass filter 202 was gradually increased as 0 cm, 1 cm, 2 cm, 5 cm, 8 cm, 10 cm, 15 cm, 20 cm, 25 cm, 30 cm, 40 cm, 50 cm, and 60 cm. At the time when each of changes in the liquid mass became less than 0.005 g/min, corresponding values (g) of the scale were respectively A0, A1, A2, A5, A8, A10, A15, A20, A25, A30, A40, A50, and A60.

<<Step (6)>>

Under such condition that there was no sample on the glass filter (blank), the height difference (cm) from the height of the intermediate position level of the thickness of the glass filter 202 was gradually increased as 0 cm, 1 cm, 2 cm, 5 cm, 8 cm, 10 cm, 12 cm, 20 cm, 25 cm, 30 cm, 40 cm, and 60 cm, without the piston and the weight. At the time when each of changes in the liquid mass became less than 0.005 g/min, corresponding values (g) of the scale were respectively B0, B1, B2, B5, B8, B12, B20, B25, B30, B40, B50, and B60.

<<Step (7)>>

In the present invention, on the basis of a value (A60−B60), values (each indicated by an absolute value (cm) since a value of the actual scale was minus) each of which was obtained by subtracting (A60−B60) from the liquid mass at each height (for example, from A30−B30) were void water amounts at heights of 0 cm, 1 cm, 2 cm, 5 cm, 8 cm, 10 cm, 15 cm, 20 cm, 25 cm, 30 cm, 40 cm, 50 cm, and 60 cm.

<<Step (8)>>

Next, a cumulative void water content was calculated from the void water amount at each height. As described above, liquid at the height of 0 cm was retained by a void whose void radius (capillary radius) was 1485 μm, liquid at the height of 1 cm was retained by a void whose void radius was 743 μm, liquid at the height of 2 cm was retained by a void whose void radius was 297 μm, liquid at the height of 5 cm was retained by a void whose void radius was 186 μm, liquid at the height of 8 cm was retained by a void whose void radius was 149 μm, liquid at the height of 10 cm was retained by a void whose void radius was 99.0 μm, liquid at the height of 15 cm was retained by a void whose void radius was 74.3 μm, liquid at the height of 20 cm was retained by a void whose void radius was 59.4 μm, liquid at the height of 25 cm was retained by a void whose void radius was 49.5 μm, liquid at the height of 30 cm was retained by a void whose void radius was 37.1 μm, liquid at the height of 40 cm was retained by a void whose void radius was 29.7 μm, liquid at the height of 50 cm was retained by a void whose void radius was 24.8 μm, and liquid at the height of 60 cm passed through a void whose void radius (capillary radius) was 24.8 μm, and the cumulative void water contents at respective heights and respective capillary radiuses were plotted on a logarithmic probability paper.

A void radius (d50) corresponding to 50% of the cumulative void water content of the graph was calculated, and the calculated value was used as a pressurized void average radius index (μm) of the sample. Further, a logarithmic standard deviation (σζ) of a distribution thereof was calculated from the cumulative void water content at each height in accordance with the following expression.

Pressurized Void Average Radius Index $$\sigma\zeta = 0.5 \times \ln(X2/X1)$$

where X1 represents a void radius at the time of R=84.1% and X2 represents a void radius at the time of R=15.9%.

Note that, the heights (0 cm to 50 cm) directly indicative of 84.1% and 15.9% may be suitably adjusted without plotting the values onto the logarithmic probability paper so as to carry out calculation.

<<Step (9)>>

As standard samples for confirming the measured values, spherical glass beads whose diameter was 350 to 500 μm and spherical glass beads whose diameter was 1000 to 1180 μm were used so as to calculate pressurized void average radius indexes (μm) in accordance with the foregoing method. As a result, the indexes were respectively 86 (μm) and 217 (μm).

<(b) Shape-Particle Size Distribution Logarithmic Standard Deviation (σζ)>

The water absorbing agent (or the water absorbent resin particles) was sieved by using JIS standard sieves (JIS Z8801-1 (2000)) respectively having mesh sizes of 850 μm, 710 μm, 600 μm, 500 μm, 425 μm, 300 μm, 212 μm, 150 μm, 45 μm, and the like, and a residual percentage R was plotted on a logarithmic probability paper.

Note that, in case where the water absorbing agent included water absorbent resin whose particle diameter exceeded 850 μm, a commercial JIS standard sieve whose mesh size exceeded 850 μm was used. Then, the logarithmic standard deviation (σζ) is represented by the following expression. As a value of σζ is smaller, the particle diameter distribution is narrower.

$$\sigma\zeta = 0.5 \times \ln(X2/X1)$$

where X1 is a particle diameter in case where R=84.1 wt % and X2 is a particle diameter in case where R=15.9 wt %.

In measuring the logarithmic standard deviation (σζ) of the particle diameter and the particle size distribution, classification was carried out as follows. 10 g of the water absorbent resin particles or the water absorbing agent was put through a JIS standard sieve (THE IIDA TESTING SIEVE; internal diameter: 8 cm), and was classified for 5 minutes by using a sieve shaker (IIDA SIEVE SHAKER, TYPE ES-65, SER. No. 0501).

<(b) Shape-Mass Average Particle Diameter (D50)>

The water absorbing agent (or the water absorbent resin particles) was sieved on the JIS standard sieve, and a residual percentage R was plotted on a logarithmic probability paper, thereby reading a mass average particle diameter (D50).

<(c) Centrifuge Retention Capacity (CRC)>

W (g) (about 0.20 g) of the water absorbing agent (or the water absorbent resin particles) obtained in below-described Examples and Comparative Examples was evenly contained in a bag (85 mm×60 mm: made of a nonwoven fabric in compliance with EDANA ERT 441.1-99). Then, the bag was sealed. Thereafter, the bag was soaked in 0.90 mass % physiological saline water whose temperature had been adjusted to 25±2° C., and was withdrawn 30 minutes later. By using a centrifuge separator (small-size centrifuge machine made by KOKUSAN Corporation: model type is H-122), the bag was drained for three minutes at a centrifugal force of 250 G (250×9.81 m/s$^2$), and a mass W2 (g) of the bag was measured. Further, the same operation was performed without using the water absorbing agent or the water absorbent resin particles, and a mass W1 (g) was measured. Then, from the masses W, W1, and W2, a centrifuge retention capacity (CRC) (g/g) was calculated according to the following expression.

$$(CRC)\ (g/g) = \{(mass\ W2\ (g) - mass\ W1\ (g))/W\ (g)\} - 1$$

<(d) Absorbency Against Pressure (AAP)>

The absorbency against pressure (AAP) represents an absorbency at which a physiological saline water (0.90 mass % sodium chloride aqueous solution) is absorbed for 60 minutes at 4.83 kPa.

By using a device shown in FIG. 1, the absorbency against pressure (AAP) was measured.

On a bottom of a plastic supporting cylinder 100 having a 60 mm internal diameter, a metal gauze 101 of stainless-steel 400 mesh (mesh size of 38 μm) was fusion-bonded. Then, under a condition of a room temperature (23.0±2.0° C.) and 50 RH % relative humidity, 0.90 g of water absorbent resin 102 was evenly spread on the mesh. Subsequently, a piston 103 and a load 104 were placed in this order on the water absorbent resin 102. The piston 103 and the load 104 were so adjusted as to evenly apply a 4.83 kPa (0.7 psi) load onto the water absorbent resin 102. Then, a mass Wa (g) of this measurement set was measured. Note that, external diameters of the piston 103 and the load 104 were slightly smaller than 60 mm which was the internal diameter of the supporting cylinder 100, so that there is little gap between the piston 103 and the supporting cylinder 100, and upward and downward movements of the piston 103 and the load 104 would not be hampered.

Inside a petri dish 105 having a 150 mm diameter, a glass filter 106 (product of Sougo Rikagaku Glass Seisakusho Co., Ltd.; diameter of fine pores: 100 to 120 μm) having a 90 mm diameter and 5 mm thickness was placed. Thereafter, a physiological saline water (0.9 wt % sodium chloride aqueous solution) 108 whose temperature had been adjusted to 20° C. to 25° C. was added until it reached a level of an upper surface of the glass filter 106. Then, a piece of filter paper 107 having a 90 mm diameter was placed thereon, so that an entire surface of the filter paper 107 was wetted. An excess of the 0.90 wt % saline 108 was removed.

The measuring device set was placed on the wet filter paper 107. Then, the water absorbent resin 102 was made to absorb the 0.90 mass % saline 108 for a predetermined time period under the load. One hour later, the measuring device set having absorbed the 0.90 mass % saline 108 was lifted, and a mass Wb (g) thereof was measured. From the masses Wa and Wb, the absorbency against pressure (AAP) (g/g) was calculated according to the following expression.

$$AAP\ (g/g) = [Wb\ (g) - Wa\ (g)]/weight\ of\ water\ absorbing\ agent$$

<(c) FSR>

On the basis of U.S. Pat. No. 6,849,665B1, the free swell rate (FSR) was measured by using a physiological saline water.

<(f) Extractable Content>

On the basis of WO2005-92956, the extractable content was measured by using a physiological saline water.

<(g) Moisture Content>

The moisture content of the water absorbing agent (or the water absorbent resin particles) was calculated from a drying loss as follows.

W (g) (about 2.00 g) of the water absorbing agent was spread on an aluminum cup whose bottom diameter was 52 mm, and a total mass W6 (g) of the water absorbing agent (or the water absorbent resin particles) and the aluminum cup was measured. Thereafter, the aluminum cup on which the water absorbing agent (or the water absorbent resin particles) had been spread was dried for three hours by a stationary dryer whose atmospheric temperature was 180° C. After retrieving the aluminum cup from the dryer, the aluminum cup was placed in a desiccator of room temperature (25° C.±2° C.) in a still manner. Then, the water absorbing agent (or the water absorbent resin particles) was cooled in a natural manner. Thereafter, a total mass W7 (g) of the dried water absorbing agent (or water absorbent resin particles) and the aluminum cup was measured. Then, a moisture content (mass %) was calculated from W, W6, and W7, according to the following expression.

$$Moisture\ content\ (mass\ \%) = \{(W6\ (g) - W7\ (g))/W\ (g)\} \times 100$$

<(h) Bulk Specific Gravity>

On the basis of U.S. Pat. No. 6,562,879, the bulk specific gravity was measured.

Example 1

0.4 g of polyethyleneglycoldiacrylate (average additional mol number of ethyleneoxide was 9) and 5.0 g of hydroxyethylcellulose SP850 (DAICEL CHEMICAL INDUSTRIES, LTD.) were dissolved in 334 g (monomer concentration was 35 mass %) of sodium acrylate aqueous solution which had been obtained by mixing acrylic acid, sodium acrylate aqueous solution, and deionized water and whose neutralization ratio was 75 mol %, thereby preparing a monomer aqueous solution.

780 g of cyclohexane was put into a 2-liter four-inlet separable flask equipped with a stirrer, a reflux condenser, a thermometer, a nitrogen gas conduit, and a water bath, and 4.0 g of sucrose fatty acid ester F-50 (DAI-ICHI KOGYO SEIYAKU CO., LTD: HLB=6) was added thereto, and the resultant was stirred at 240 rpm so as to be dispersed. An internal gas of the flask was replaced with nitrogen gas, and then its temperature was raised to 70° C. The monomer aqueous solution having been prepared in the foregoing manner was poured into the resultant. Thereafter, reversed phase suspension polymerization was initiated. 15 minutes later, the temperature reached the polymerization reaction peak temperature of 74° C. The resultant was kept for 30 minutes at a water bath temperature of 70° C. after the peak, and then the water bath temperature was set to 90° C., thereby carrying out dehydration until a moisture content of resin particles generated by azeotropy with cyclohexane became 30%.

After the dehydration, the stirring operation was stopped, so that the resin particles settled down to a bottom of the flask. The resin particles having settled down were separated by decantation. The resultant resin particles were spread on a stainless container, and the spread resin particles were heated at 150° C. for two hours, and adhering cyclohexane and a slight amount of water were removed, thereby obtaining water absorbent resin particles (a1) which were in a spherical-single-grain manner.

3.0 parts by mass of a first surface cross-linking agent aqueous solution containing 0.5 parts by mass of propyleneglycol, 0.3 parts by mass of 1,4-butanediol, and 2.7 parts by mass of water was sprayed so as to be mixed with 100 parts by mass of the water absorbent resin particles (a1). The mixture was subjected to a heating treatment at 180° C. for one hour with a hot air dryer, thereby obtaining water absorbent resin particles (b1). Thereafter, 1.22 parts by mass of a second surface cross-linking agent aqueous solution containing 0.5 parts by mass of aluminum sulfate and 0.6 parts by mass of water was sprayed so as to be mixed with 100 parts by mass of the water absorbent resin particles (b1). The mixture was subjected to a heating treatment at 60° C. for one hour with a hot air dryer, thereby obtaining a water absorbing agent (Ex1) which was in a spherical manner. Properties of the water absorbing agent (Ex1) are shown in Tables 1 to 3.

Comparative Example 1

8.25 parts by mass of polyethyleneglycoldiacrylate (average additional mol number of ethyleneoxide was 9) was dissolved in 5460 parts by mass of sodium acrylate aqueous solution which had been obtained by mixing acrylic acid, sodium acrylate aqueous solution, and deionized water and whose neutralization ratio was 75 mol %, thereby preparing a reaction solution. Subsequently, the reaction solution was supplied to a reaction container formed by providing a lid on a 10-litter stainless double-arm kneader equipped with two sigma vanes and a jacket, and dissolved oxygen was removed from the reaction solution by means of nitrogen gas while keeping the reaction solution at 25° C.

Subsequently, 29.0 parts by mass of sodium persulfate 10 mass % aqueous solution and 4.4 parts by mass of L-ascorbic acid 1 mass % aqueous solution were added while stirring the reaction solution, so that polymerization was initiated about one minute later. In 15 minutes after initiation of the polymerization, a temperature thereof became a polymerization peak temperature of 92° C. In 40 minutes after the initiation of the polymerization, a hydrogel polymer was retrieved. The resultant hydrogel polymer was particles fragmented so as to have a particle size ranging from 1 to 4 mm. The fragmented hydrogel polymer particles were spread on a metal gauze of 50 mesh (mesh size was 300 μm), and the spread hydrogel polymer particles were dried by hot air at 180° C. for 40 minutes. Subsequently, the dried resultant was pulverized by a roll mill, and the pulverized resultant was classified by metal gauzes whose mesh sizes were respectively 850 μm and 150 μm, thereby obtaining irregularly-pulverized water absorbent resin particles (Ca1). A centrifuge retention capacity (CRC) of the resultant water absorbent resin particles (Ca1) was 33 g/g. Further, a particle size distribution of the water absorbent resin particles (Ca1) is shown in Table 1 and Table 2.

3.5 parts by mass of a first surface cross-linking agent aqueous solution containing 0.5 parts by mass of propyleneglycol, 0.3 parts by mass of 1,4-butanediol, and 2.7 parts by mass of water was sprayed so as to be mixed with 100 parts by mass of the water absorbent resin particles (Ca1). The mixture was subjected to a heating treatment at 180° C. for one hour with a hot air dryer, thereby obtaining water absorbent resin particles (C-Ex1).

The resultant water absorbent resin particles were regarded as a comparative water absorbing agent (C-Ex1) of the present invention, and properties thereof are shown in Tables 1 to 3.

Comparative Example 2

1.22 parts by mass of a second surface cross-linking agent aqueous solution containing 0.5 parts by mass of aluminum sulfate and 0.6 parts by mass of water was sprayed so as to be mixed with 100 parts by mass of the water absorbent resin particles (C-Ex1) obtained in Comparative Example 1. The mixture was subjected to a heating treatment at 60° C. for one hour with a hot air dryer, thereby obtaining water absorbent resin particles (C-Ex2).

The resultant water absorbent resin particles were regarded as a comparative water absorbing agent (C-Ex2) of the present invention, and properties thereof are shown in Tables 1 to 3.

Comparative Example 3

0.5 parts by mass of Aerosil™ 200 (product of Nippon Aerosil Co., Ltd.) was dry-blended with 100 parts by mass of the water absorbent resin particles (C-Ex1) obtained in Comparative Example 1, and the resultant mixture was made to pass through a sieve whose mesh size was 850 μm, thereby obtaining a comparative water absorbing agent (C-Ex3) of the present invention. Properties of the comparative water absorbing agent (C-Ex3) were measured and are shown in Tables 1 to 3.

Comparative Example 4

0.5 parts by mass of Aerosil® 200 (product of Nippon Aerosil Co., Ltd.) was dry-blended with 100 parts by mass of the water absorbent resin particles (C-Ex2) obtained in Comparative Example 2, and the resultant mixture was made to pass through a sieve whose mesh size was 850 μm, thereby obtaining a comparative water absorbing agent (C-Ex4).

Properties of the comparative water absorbing agent (C-Ex4) were measured and are shown in Tables 1 to 3.

Comparative Example 5

12.0 parts by mass of polyethyleneglycoldiacrylate (average additional mol number of ethyleneoxide was 9) was dissolved in 5452 parts by mass of sodium acrylate aqueous solution (monomer concentration was 41 mass %) which had been obtained by mixing acrylic acid, sodium acrylate aqueous solution, and deionized water and whose neutralization ratio was 71 mol %, thereby preparing a reaction solution. Subsequently, the reaction solution was supplied to a reaction container formed by providing a lid on a 10-litter stainless double-arm kneader equipped with two sigma vanes and a jacket, and dissolved oxygen was removed from the reaction solution by means of nitrogen gas while keeping the reaction solution at 25° C.

Subsequently, 31 parts by mass of sodium persulfate 10 mass % aqueous solution and 4.6 parts by mass of L-ascorbic acid 1 mass % aqueous solution were added while stirring the reaction solution, so that polymerization was initiated about one minute later. In 15 minutes after initiation of the polymerization, a temperature thereof became a polymerization peak temperature of 92° C. In 40 minutes after the initiation of the polymerization, a hydrogel polymer was retrieved. The resultant hydrogel polymer was particles fragmented so as to have a particle size ranging from 1 to 4 mm. The fragmented hydrogel polymer particles were spread on a metal gauze of 50 mesh (mesh size was 300 μm), and the spread hydrogel polymer particles were dried by hot air at 180° C. for 45 minutes. Subsequently, the dried resultant was pulverized by a roll mill, and the pulverized resultant was classified by metal gauzes whose mesh sizes were respectively 850 μm and 150 μm, thereby obtaining irregularly-pulverized water absorbent resin particles (Ca5). A centrifuge retention capacity (CRC) of the resultant water absorbent resin particles (Ca5) was 32 g/g.

3.9 parts by mass of a first surface cross-linking agent aqueous solution containing 0.6 parts by mass of propyleneglycol, 0.3 parts by mass of 1,4-butanediol, and 3.0 parts by mass of water was sprayed so as to be mixed with 100 parts by mass of the water absorbent resin particles (Ca5). The mixture was subjected to a heating treatment at 180° C. for one hour with a hot air dryer, thereby obtaining water absorbent resin particles (Cb5). Thereafter, 1.22 parts by mass of a second surface cross-linking agent aqueous solution containing 0.5 parts by mass of aluminum sulfate and 0.6 parts by mass of water was sprayed so as to be mixed with 100 parts by mass of the water absorbent resin particles (Cb5). The mixture was subjected to a heating treatment at 60° C. for one hour with a hot air dryer, thereby obtaining a comparative water absorbing agent (C-Ex5) of the present invention.

Properties of the comparative water absorbing agent (C-Ex5) were measured and are shown in Tables 1 to 3.

Comparative Example 6

92 g (1.02 mol) of 80 mass % acrylic acid aqueous solution was poured in a 500-mL conical flask, and 146.0 g of 21.0 mass % sodium hydrate aqueous solution was dropped while cooling the acrylic acid aqueous solution by ice, and 75 mol % of acrylic acid was neutralized, thereby preparing acrylic acid partially neutralized salt aqueous solution whose monomer concentration was 38 mass %. 9.2 mg (53 μmol) of ethyleneglycoldiglycidylether serving as an internal cross-linking agent and 92 mg (0.34 mili mol) of potassium sulfate serving as a radical polymerization initiator were added to the resultant acrylic acid partially neutralized salt aqueous solution, thereby preparing a monomer aqueous solution (A) for first stage polymerization.

While, 340 g (500 mL) of n-heptane and 0.92 g [HLB value of 3.0) of sucrose fatty acid ester serving as a surfactant were added into a 2-litter five-inlet cylindrical round-bottom flask equipped with a stirrer, a two-paddle vane, a reflux condenser, a dropping funnel, and a nitrogen gas conduit so as to dissolve n-heptane, and then an internal temperature was set to 35° C. Thereafter, the aforementioned monomer aqueous solution (A) for first stage polymerization was added and the temperature was kept at 35° C., and the resultant was suspended while being stirred, and an inside of the system was replaced with nitrogen gas. Thereafter, the temperature was raised to 70° C., thereby carrying out first-stage reversed phase suspension polymerization.

Besides, 92 g (1.02 mol) of 80 mass % acrylic acid aqueous solution was poured in a 500-mL conical flask, and 146.0 g of 21.0 mass % sodium hydrate aqueous solution was dropped while cooling the acrylic acid aqueous solution by ice, and 75 mol % of acrylic acid was neutralized, thereby preparing acrylic acid partially neutralized salt aqueous solution whose monomer concentration was 38 mass %. 9.2 mg (53 μmol) of ethyleneglycoldiglycidylether serving as an internal cross-linking agent and 92 mg (0.34 mili mol) of potassium sulfate serving as a radical polymerization initiator were added to the resultant acrylic acid partially neutralized salt aqueous solution, thereby preparing a monomer aqueous solution (B) for second-stage polymerization.

After finishing the first-stage reversed phase polymerization, the polymerized slurry was cooled to 23° C., and the monomer aqueous solution (B) for second-stage reversed phase suspension polymerization was dropped into the system with the surfactant precipitated, and the resultant was stirred for 30 minutes while keeping the temperature at 23° C. and the inside of the system was sufficiently replaced with nitrogen gas at the same time. Thereafter, the temperature was raised to 70° C., thereby carrying out the second-stage reversed phase suspension polymerization.

After finishing the reversed phase suspension polymerization, the resultant was heated again, thereby removing 250 g of water from an azeotropic mixture of n-heptane and water. Thereafter, 368 mg (2.11 mili mol) of ethyleneglycoldiglycidylether was added as a post-cross-linking agent so as to carry out post cross-linking reaction in the presence of 45 g of water at 80° C. for two hours. After the cross-linking reaction, n-heptane and water were thermally distilled from the system, thereby obtaining water absorbent resin particles (C-Ex6) which were in a spherical-granulated-particle manner (granulated spherical particles in a bunch-of-grapes-manner).

Comparative Example 7

5.3 parts by mass of a first surface cross-linking agent aqueous solution containing 0.8 parts by mass of propyleneglycol, 0.5 parts by mass of 1,4-butanediol, and 4.0 parts by mass of water was sprayed so as to be mixed with 100 parts by mass of the water absorbent resin particles (C-Ex6) obtained in Comparative Example 6. The mixture was subjected to a heating treatment at 185° C. for two hours with a hot air dryer, thereby obtaining water absorbent resin particles.

The resultant water absorbent resin particles were regarded as a comparative water absorbing agent (C-Ex7) of the present invention, and properties thereof were measured and are shown in Tables 1 to 3.

Example 2

1.22 parts by mass of a second surface cross-linking agent aqueous solution containing 0.5 parts by mass of aluminum sulfate and 0.6 parts by mass of water was sprayed so as to be mixed with 100 parts by mass of the water absorbent resin particles (C-Ex7) obtained in Comparative Example 7. The mixture was subjected to a heating treatment at 60° C. for one hour with a hot air dryer, thereby obtaining a water absorbing agent (Ex2) which was in a spherical-granulated-particle manner. Properties of the resultant water absorbing agent (Ex2) were measured and are shown in Tables 1 to 3. Note that, a free swell rate (FSR) of the water absorbing agent (Ex2) was 0.46 g/g/s.

Example 3

12.0 parts by mass of polyethyleneglycoldiacrylate (average additional mol number of ethyleneoxide was 9) was dissolved in 5452 parts by mass of sodium acrylate aqueous solution (monomer concentration was 41 mass %) which had been obtained by mixing acrylic acid, sodium acrylate aqueous solution, and deionized water and whose neutralization ratio was 71 mol %, thereby preparing a reaction solution. Subsequently, the reaction solution was supplied to a reaction container formed by providing a lid on a 10-litter stainless double-arm kneader equipped with two sigma vanes and a jacket, and dissolved oxygen was removed from the reaction solution by means of nitrogen gas while keeping the reaction solution at 25° C.

Subsequently, 31 parts by mass of sodium persulfate 10 mass % aqueous solution and 4.6 parts by mass of L-ascorbic acid 1 mass % aqueous solution were added while stirring the reaction solution, so that polymerization was initiated about one minute later. In 15 minutes after initiation of the polymerization, a temperature thereof became a polymerization peak temperature of 92° C. In 40 minutes after the initiation of the polymerization, a hydrogel polymer was retrieved. The resultant hydrogel polymer was particles fragmented so as to have a particle size ranging from 1 to 4 mm. The fragmented hydrogel polymer particles were spread on a metal gauze of 50 mesh (mesh size was 300 μm), and the spread hydrogel polymer particles were dried by hot air at 180° C. for 45 minutes. Subsequently, the dried resultant was pulverized by a roll mill, and the pulverized resultant was classified by metal gauzes whose mesh sizes were respectively 850 μm and 300 μm, thereby obtaining irregularly-pulverized water absorbent resin particles.

100 g of the resultant water absorbent resin particles were placed in a homogenizer (high-speed homogenizer, product of NIPPON SEIKI CO., LTD., Model No. MX-7), and the water absorbent resin particles were ground at a rotational frequency of 6,000 rpm for five minutes. The resultant water absorbent resin particles were classified by metal gauzes whose mesh sizes were respectively 850 μm and 300 μm, thereby obtaining ground water absorbent resin particles.

3.5 parts by mass of a first surface cross-linking agent aqueous solution containing 0.5 parts by mass of propyleneglycol, 0.3 parts by mass of 1,4-butanediol, and 2.7 parts by mass of water was sprayed so as to be mixed with 100 parts by mass of the ground water absorbent resin particles. The mixture was subjected to a heating treatment at 185° C. for one hour with a hot air dryer, thereby obtaining water absorbent resin particles. Thereafter, 1.22 parts by mass of a second surface cross-linking agent aqueous solution containing 0.5 parts by mass of aluminum sulfate and 0.6 parts by mass of water was sprayed so as to be mixed with 100 parts by mass of the water absorbent resin particles. The mixture was subjected to a heating treatment at 60° C. for one hour with a hot air dryer, thereby obtaining an irregularly-pulverized water absorbing agent (Ex3) of the present invention.

Properties of the resultant water absorbing agent (Ex3) were measured and are shown in Tables 1 to 3.

TABLE 1

| | Water absorbing agent | 850 μm or more | 710 μm or more less than 850 μm | 600 μm or more less than 710 μm | 500 μm or more less than 600 μm | 425 μm or more less than 500 μm | 300 μm or more less than 425 μm | 212 μm or more less than 300 μm | 150 μm or more less than 212 μm | 45 μm or more less than 150 μm | less than 45 μm |
|---|---|---|---|---|---|---|---|---|---|---|---|
| Example 1 | a 1 | 0.0 | 0.2 | 2.2 | 2.2 | 21.6 | 39.9 | 16.9 | 8.6 | 8.1 | 0.3 |
| Example 1 | Ex 1 | 0.0 | 0.2 | 2.2 | 2.2 | 21.7 | 40.2 | 17.2 | 8.7 | 7.5 | 0.1 |
| Example 2 | Ex 2 | 0.0 | 0.2 | 2.1 | 5.8 | 17.8 | 44.1 | 22.5 | 5.8 | 1.6 | 0.1 |
| Example 3 | Ex 3 | 0.0 | 3.2 | 24.3 | 22.2 | 30.5 | 19.6 | 0.2 | 0.0 | 0.0 | 0.0 |
| Comparative Example 1 | Ca 1 | 0.0 | 2.5 | 25.5 | 18.3 | 14.9 | 21.7 | 11.0 | 4.0 | 2.0 | 0.1 |
| Comparative Example 1 | C-Ex 1 | 0.0 | 2.5 | 25.3 | 18.8 | 15.1 | 21.8 | 11.8 | 3.4 | 1.2 | 0.1 |
| Comparative Example 2 | C-Ex 2 | 0.0 | 2.6 | 25.9 | 21.3 | 16.4 | 21.3 | 8.3 | 2.9 | 1.3 | 0.1 |
| Comparative Example 3 | C-Ex 3 | 0.0 | 2.5 | 25.3 | 18.8 | 15.1 | 21.8 | 11.8 | 3.4 | 1.2 | 0.1 |
| Comparative Example 4 | C-Ex 4 | 0.0 | 2.6 | 25.9 | 21.3 | 16.4 | 21.3 | 8.3 | 2.9 | 1.3 | 0.1 |
| Comparative Example 5 | C-Ex 5 | 0.0 | 0.0 | 0.3 | 4.9 | 13.3 | 41.7 | 30.9 | 7.2 | 1.6 | 0.1 |
| Comparative Example 6 | C-Ex 6 | 0.0 | 0.2 | 2.1 | 5.5 | 17.3 | 43.8 | 23.2 | 6.1 | 1.8 | 0.0 |
| Comparative Example 7 | C-Ex 7 | 0.0 | 0.2 | 2.1 | 5.6 | 17.4 | 43.9 | 23.0 | 6.0 | 1.8 | 0.0 |

TABLE 2

| | Water absorbing agent | D50 (μm) | σζ | Ratio of particles whose particle diameter is less than 150 μm | Bulk specific gravity (g/ml) |
|---|---|---|---|---|---|
| Example 1 | a 1 | 344 | 0.40 | 8.4 | 0.88 |
| Example 1 | Ex 1 | 345 | 0.38 | 7.6 | 0.88 |
| Example 2 | Ex 2 | 351 | 0.30 | 1.7 | 0.72 |
| Example 3 | Ex 3 | 499 | 0.21 | 0.0 | 0.74 |
| Comparative Example 1 | Ca 1 | 481 | 0.39 | 2.1 | 0.68 |
| Comparative Example 1 | C-Ex 1 | 482 | 0.38 | 1.3 | 0.68 |
| Comparative Example 2 | C-Ex 2 | 499 | 0.34 | 1.4 | 0.68 |
| Comparative Example 3 | C-Ex 3 | 482 | 0.38 | 1.3 | 0.66 |
| Comparative Example 4 | C-Ex 4 | 499 | 0.34 | 1.4 | 0.66 |

TABLE 2-continued

| Water absorbing agent | D50 (μm) | σζ | Ratio of particles whose particle diameter is less than 150 μm | Bulk specific gravity (g/ml) |
|---|---|---|---|---|
| Comparative Example 5 | C-Ex 5 | 324 | 0.30 | 1.7 | 0.67 |
| Comparative Example 6 | C-Ex 6 | 348 | 0.31 | 1.8 | 0.72 |
| Comparative Example 7 | C-Ex 7 | 348 | 0.31 | 1.8 | 0.72 |

TABLE 3

| | Water absorbing agent | CRC (g/g) | AAP (g/g) | Pressurized void average radius index (μm) | σζ of pressurized void radius index | Moisture content (%) |
|---|---|---|---|---|---|---|
| Example 1 | Ex 1 | 26.4 | 23.0 | 210 | 1.25 | 2.9 |
| Example 2 | Ex 2 | 26.8 | 20.1 | 170 | — | 1.2 |
| Example 3 | Ex 3 | 26.2 | 23.0 | 110 | 0.86 | 0.9 |
| Comparative Example 1 | C-Ex 1 | 29.4 | 24.6 | 68.1 | 1.27 | 3.0 |
| Comparative Example 2 | C-Ex 2 | 29.3 | 23.8 | 74.1 | 1.34 | 3.2 |
| Comparative Example 3 | C-Ex 3 | 29.2 | 23.2 | 72.9 | 0.98 | 3.0 |
| Comparative Example 4 | C-Ex 4 | 29.1 | 21.8 | 80.7 | 1.47 | 3.2 |
| Comparative Example 5 | C-Ex 5 | 28.0 | 23.4 | 56.1 | 0.78 | 3.2 |
| Comparative Example 6 | C-Ex 6 | 34.7 | 14.1 | 80.1 | 1.14 | 3.1 |
| Comparative Example 7 | C-Ex 7 | 27.3 | 23.3 | 96.6 | — | 0.5 |

INDUSTRIAL APPLICABILITY

In case of using the particulate water absorbing agent obtained by the present invention in a thin absorbent core of a diaper or the like with high concentration, it is possible to provide an absorbent core which has extremely excellent absorbing performance, particularly, has excellent liquid permeability.

The invention claimed is:

1. A water absorbing agent, comprising water absorbent resin particles which are obtained by polymerizing a water-soluble ethylenic unsaturated monomer and which internally include a cross-linked structure, wherein a pressurized void average radius index is 140 μm or more,
    where the pressurized void average radius index is a swollen gel void radius (d50) corresponding to 50% of a cumulative void water content in a physiological saline water under a load of 2.07 kPa, and
    the water absorbent resin particles each have a spherical or substantially spherical shape and the water absorbing agent contains a pressurized void average radius index enhancing agent selected from the group consisting of a multivalent metal compound, inorganic fine particles and a polycation polymer compound.

2. A water absorbing agent comprising water absorbent resin particles which are obtained by polymerizing a water-soluble ethylenic unsaturated monomer and which internally include a cross-linked structure, wherein 90 wt % or more of the water absorbing agent are particles whose particle diameter ranges from 150 to 850 μm, and a pressurized void average radius index is 100 μm or more,
    where the pressurized void average radius index is a swollen gel void radius (d50) corresponding to 50% of a cumulative void water content in a physiological saline water under a load of 2.07 kPa, and
    the water absorbent resin particles each have a spherical or substantially spherical shape and the water absorbing agent contains a pressurized void average radius index enhancing agent selected from the group consisting of a multivalent metal compound, inorganic fine particles and a polycation polymer compound.

3. A water absorbing agent according to claim 2, wherein 90 wt % or more of the water absorbing agent obtained by reversed phase suspension polymerization are particles whose particle diameter ranges from 150 to 850 μm.

4. The water absorbing agent as set forth in any one of claims 1 to 3, wherein the water absorbing agent is a particulate and an absorbency against pressure (AAP) is 10 g/g or more where the pressure is 4.83 kPa.

5. The water absorbing agent as set forth in claim 1, wherein a surface of the water absorbent resin particles is cross-linked.

6. The water absorbing agent as set forth in claim 1, wherein a mass average particle diameter (D50) ranges from 200 to 500 μm, and a logarithmic standard deviation (σζ) of a particle size distribution ranges from 0.25 to 0.45, and a bulk specific gravity (g/ml) ranges from 0.72 to 1.00.

7. The water absorbing agent as set forth in claim 1, wherein an absorbency against pressure (AAP) ranges from 20 g/g to 29 g/g where the pressure is 4.83 kPa, and a difference between a centrifuge retention capacity (CRC) and the absorbency against pressure (AAP) is 7 g/g or less.

8. The water absorbing agent as set forth in claim 1, wherein the water absorbent resin is a particulate.

9. The water absorbing agent as set forth in claim 8, wherein the water absorbing agent is in a granulated manner.

10. A method for producing a water absorbing agent, comprising the steps of:
    cross-linking and polymerizing an unsaturated monomer aqueous solution containing acrylic acid and/or salt thereof as a main component in the presence of an internal cross-linking agent so as to obtain water absorbent resin particles;
    drying the water absorbent resin particles after the step of cross-linking and polymerizing the unsaturated monomer aqueous solution, so as to satisfy the following conditions (a) to (c) in the water absorbent resin particles; and adding to the water absorbent resin particles an agent for enhancing a pressurized void average radius index in an effective amount to provide a pressurized void average radius index of 100 μm or more, and where the pressurized void average radius index is a swollen gel void radius (d50) corresponding to 50% of a cumulative void water content in a physiological saline water under a load of 2.07 kPa, wherein (a) a mass average particle diameter (D50) ranges from 200 to 500 μm,
(b) a logarithmic standard deviation (σζ) of a particle size distribution ranges from 0.25 to 0.45, and
(c) a bulk specific gravity (g/ml) ranges from 0.72 to 1.00, and the water absorbent resin particles each having a spherical shape or substantially spherical shape, and where the agent for enhancing the pressurized void average radius index is selected from the group consisting of a multivalent metal compound, inorganic fine particles and a polycation polymer compound.

11. The method as set forth in claim 10, comprising the step of carrying out a surface cross-linking treatment with respect to a surface of the water absorbent resin particles after the step of drying the water absorbent resin particles.

12. A method for producing a water absorbing agent, comprising the steps of:

cross-linking and polymerizing an unsaturated monomer aqueous solution containing acrylic acid and/or salt thereof as a main component in a hydrophobic organic solvent by reversed phase suspension polymerization so as to obtain water absorbent resin particles;

drying the water absorbent resin particles;

carrying out a surface cross-linking treatment; and adding to the water absorbent resin particles an agent for enhancing a pressurized void average radius index in an effective amount to provide a pressurized void average radius index of 100 μm or more, and where the pressurized void average radius index is a swollen gel void radius (d50) corresponding to 50% of a cumulative void water content in a physiological saline water under a load of 2.07 kPa, and the water absorbent resin particles each having a spherical shape or substantially spherical shape, and where the agent for enhancing the pressurized void average radius index is selected from the group consisting of a multivalent metal compound, inorganic fine particles and a polycation polymer compound.

13. The method as set forth in claim 10, wherein 90 wt % or more of the water absorbent resin particles is particles whose particle diameter ranges from 150 to 850 μm.

14. The method as set forth in claim 10, wherein (i) a polymerizable cross-linking agent having two or more polymerizable unsaturated groups and (ii) a reactive internal cross-linking agent having two or more covalent binding groups or an ionic bonding group is used together as the internal cross-linking agent.

15. The method as set forth in claim 12, wherein the water absorbent resin particles in or after carrying out the surface cross-linking treatment satisfy the following conditions (a) to (c), where (a) a mass average particle diameter (D50) ranges from 200 to 500 μm,
(b) a logarithmic standard deviation (σζ) of a particle size distribution ranges from 0.25 to 0.45, and
(c) a bulk specific gravity (g/ml) ranges from 0.72 to 1.00.

16. The method as set forth in claim 10, wherein the agent for enhancing a pressurized void average radius index is selected from the group consisting of bivalent, trivalent, and tetravalent metal salts.

17. An absorbing article, comprising the water absorbing agent as set forth in claim 1, wherein the absorbing article absorbs urine, feces, or blood.

18. The water absorbing agent as set forth in claim 1, wherein a logarithmic average standard deviation (σζ) of the pressurized void average radius index ranges from 0.4 to 1.4.

19. The water absorbing agent as set forth in claim 1, wherein the water absorbing agent has a free swell rate (FSR) of not less than 0.3 g/g/s and not more than 5 g/g/s.

20. The water absorbing agent as set forth in claim 2, wherein a logarithmic average standard deviation (σζ) of the pressurized void average radius index ranges from 0.4 to 1.4.

21. The water absorbing agent as set forth in claim 2, wherein the water absorbing agent has a free swell rate (FSR) of not less than 0.3 g/g/s and not more than 5 g/g/s.

22. The method of claim 10 or claim 12, wherein said agent for enhancing a pressurized void average radius index is added in an effective amount to provide a pressurized void average radius index of 140 μm or more.

23. The water absorbing agent of claim 1, wherein the multivalent metal compound is selected from the group consisting of bivalent, trivalent and tetravalent metal salts.

24. The water absorbing agent of claim 2, wherein the multivalent metal compound is selected from the group consisting of bivalent, trivalent and tetravalent metal salts.

* * * * *